United States Patent [19]

Koga et al.

[11] Patent Number: 5,412,117

[45] Date of Patent: May 2, 1995

[54] BENZOPYRAN DERIVATIVES

[75] Inventors: Hiroshi Koga, Saitama; Hiroyuki Nabata, Kanagawa, both of Japan

[73] Assignee: Chugai Seiyaku Kabushiki Kaisha, Tokyo, Japan

[21] Appl. No.: 962,215

[22] PCT Filed: Jul. 26, 1991

[86] PCT No.: PCT/JP91/01005

§ 371 Date: Jan. 26, 1993

§ 102(e) Date: Jan. 26, 1993

[87] PCT Pub. No.: WO92/02514

PCT Pub. Date: Feb. 20, 1992

[30] Foreign Application Priority Data

Jul. 27, 1990 [JP] Japan .................. 2-199738
Nov. 1, 1990 [JP] Japan .................. 2-297009
Mar. 14, 1991 [JP] Japan .................. 3-049827

[51] Int. Cl.⁶ ............................ C07D 311/58
[52] U.S. Cl. ........................... 549/404; 544/151;
544/317; 544/336; 544/376; 546/196; 548/139;
548/195; 548/251; 548/311.4; 548/525;
548/953; 548/964; 549/399; 549/405; 549/407
[58] Field of Search ............ 549/404, 405, 407

[56] References Cited

U.S. PATENT DOCUMENTS

| | | | |
|---|---|---|---|
| 3,103,519 | 9/1963 | Zaugg et al. | |
| 3,122,551 | 2/1964 | Zaug et al. | 549/405 |
| 3,156,688 | 11/1964 | Zaugg et al. | 549/405 |
| 4,935,441 | 6/1990 | Rimbault | 549/405 |
| 5,155,130 | 10/1992 | Stanton et al. | 549/407 |

FOREIGN PATENT DOCUMENTS

| | | |
|---|---|---|
| 0412939 | 2/1990 | European Pat. Off. |
| 0439265 | 11/1991 | European Pat. Off. |
| 55-85582 | 6/1980 | Japan |
| 1143875 | 6/1989 | Japan |
| 1018984 | 10/1963 | United Kingdom |
| 9014346 | 11/1990 | WIPO |

OTHER PUBLICATIONS

H. E. Zaugg, J. E. Leonard, R. W. DeNet, D. L. Arendsen, "Substituted Chromans and Tetrahydrofuro[2,3-b] benzofurans (Trapped Tetrahedral Intermediates) from 3-Phenyl-2-benzofuranones", Journal of Heterocyclic Chemistry, vol. 11, No. 5, Oct. 1974, pp.:797-802.

Primary Examiner—Robert W. Ramsuer
Attorney, Agent, or Firm—Browdy and Neimark

[57] ABSTRACT

Benzopyran derivatives represented by formula (I):

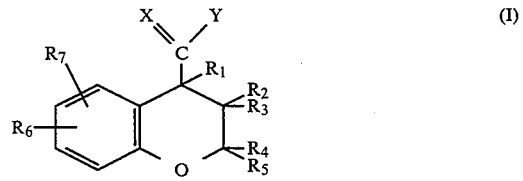

wherein X represents $=O$, $=S$, $=N-Z$ (Z represents a lower alkyl group, etc.), or $=CHNO_2$; Y represents a substituted amino group, an alkoxy group, an alkylthio group, etc., and $R_1$, $R_2$, $R_3$, $R_4$, $R_5$, $R_6$, and $R_7$ each represent a hydrogen atom, a lower alkyl group, etc., are disclosed. The benzopyran derivatives exhibit $K^+$ channel activating activities and are widely applicable as antiasthmatics, antiepileptics, and the like.

10 Claims, No Drawings

BENZOPYRAN DERIVATIVES

FIELD OF THE INVENTION

This invention relates to a novel benzopyran derivative useful as pharmaceuticals.

BACKGROUND OF THE INVENTION

Benzopyran derivatives having various pharmacological activities have hitherto been known. For example, various benzopyran derivatives in which the carbon atom at the 4-position of the benzopyran ring is directly bonded to a nitrogen atom are disclosed in Japanese Patent Application Laid-Open Nos. 60-97974, 61-47416, 63-165317, 63-196581, 63-201182, 63-303977, 64-26578, 64-38087, and 2-129184, and *Journal of Medical Chemistry*, Vol. 33, No. 6, pp. 1529–1541 (1990). The literatures report that these compounds possess antihypertensive activity and are useful for the treatment of heart diseases.

Of the benzopyran derivatives disclosed, Cromakalim having formula:

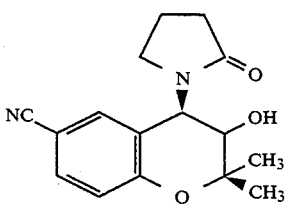

has recently attracted attention as a new type of hypotensires which acts on the K+ channel, similar to Nicorandil and Pinacidil.

Benzopyran derivatives in which the 4-carbon atom on the benzopyran ring is not bonded directly to a nitrogen atom are disclosed in Japanese Patent Application Laid-Open Nos. 63-303977 and 64-38087, *Journal of Heterocyclic Chemistry*, Vol. 11, No. 5, pp. 797–802 (1974), and *Journal of Medical Chemistry*, Vol. 33, No. 6, pp. 1529–1541 (1990).

Further, WO 90/14346 (published on Nov. 29, 1990, after the priority date of the present invention) discloses compounds having an amido group or a thioamido group at the position of the benzopyran ring thereof.

DISCLOSURE OF THE INVENTION

The inventors have conducted extensive and intensive investigations on synthesis of benzopyran derivatives with the 4-carbon atom on the benzopyran ring thereof being not bonded directly to a nitrogen atom which are equal or superior to Cromakalim in activity on the K+ channel and their activities on the K+ channel. As a result, they have found that un-reported, novel benzopyran derivatives described below possess the above-mentioned pharmacological activities and thus completed the present invention based on this finding.

The compounds according to the present invention are represented by formula (I):

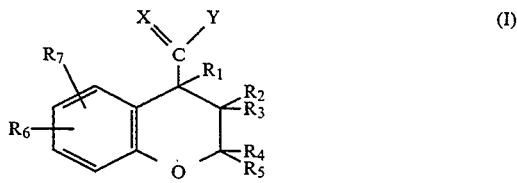

wherein X represents an oxygen atom, a sulfur atom, =N-Z, or =CHNO$_2$, wherein Z represents a hydrogen atom, a lower alkyl group, an aryl group, a hydroxyl group, a lower alkoxy group, a cyano group, a carbamoyl group, or a sulfamoyl group; Y represents —NR$_8$R$_9$, —OR$_{10}$, or —SR$_{11}$, wherein R$_8$ and R$_9$, which may be the same or different, each represent a hydrogen atom, a hydroxyl group, a lower alkoxy group, a cyano group, a substituted or unsubstituted amino group, a substituted or unsubstituted lower alkyl group, a substituted or unsubstituted unsaturated lower alkyl group, a substituted or unsubstituted cycloalkyl group, a substituted or unsubstituted aryl group, or a substituted or unsubstituted hetero-aryl group, or they are taken together with the nitrogen atom to form a substituted or unsubstituted heterocyclic ring, and R$_{10}$ and R$_{11}$ each represent a hydrogen atom, a lower alkyl group, or an aryl group; R$_1$ represent a hydrogen atom, a lower alkyl group, or an aryl group, or it is directly bonded to R$_2$ to form a single bond; R$_2$ and R$_3$, which may be the same or different, each represent a hydrogen atom or a hydroxyl group, or they are taken together to form =O, or R$_2$ is directly bonded to R$_1$ to form a single bond; R$_4$ and R$_5$, which may be the same or different, each represent a hydrogen atom or a lower alkyl group, or they are taken together to form a polymethylene group; and R$_6$ and R$_7$, which may be the same or different, each represent a hydrogen atom, a lower alkyl group, a lower haloalkyl group, a halogen atom, a lower alkoxy group, a lower haloalkoxy group, an amido group, an acylamino group, a nitro group, a cyano group, an ester group, a lower alkylsulfonyl group, or an arylsulfonyl group, or they are taken together to form =N—O—N=.

In the definition for symbols in formula (I), the term "lower alkyl group" means an alkyl group having from 1 to 6, and preferably from 1 to 4, carbon atoms. Examples of such a lower alkyl group are methyl, ethyl, n-propyl, i-propyl, n-butyl, i-butyl, sec-butyl, and t-butyl groups.

The term "aryl group" means a monovalent substituent derived from aromatic hydrocarbons by removing one hydrogen atom therefrom. Specific examples of such an aryl group are phenyl, tolyl, xylyl, biphenyl, naphthyl, anthryl, and phenathryl group, with a phenyl group being particularly preferred. The carbon atom(s) on the ring of the aryl group may be substituted with one or more groups, e.g., a halogen atom, a lower alkyl group, an amino group, a nitro group, and a trifluoromethyl group. The term "hetero-aryl group" means an aryl group containing a hereto atom. Specific examples of such a hetero-aryl group are pyridyl, pyrimidinyl, thiazolyl, oxazolyl, imidazolyl, thiadiazolyl, and tetrazolyl groups. These hetero-aryl groups may have substituent(s) on the ring thereof.

The term "lower alkoxy group" means an alkoxy group having from 1 to 6, and preferably from 1 to 4, carbon atoms. Examples of such a lower alkoxy group are methoxy, ethoxy, n-propoxy, i-propoxy, n-butoxy, i-butoxy, sec-butoxy, and t-butoxy groups.

The term "halogen atom" includes chlorine, bromine, fluorine, and iodine atoms, with a chlorine atom being particularly preferred.

The term "cycloalkyl group" preferably includes those having from 3 to 8 carbon atoms, e.g., cyclopropyl, cyclobutyl, cyclopentyl, and cyclohexyl groups.

The term "nitrogen-containing heterocyclic ring" includes aziridinyl, azetidinyl, pyrrolidinyl, piperidinyl, piperazyl, and morpholino groups.

Substituents which may be on these groups include a halogen atom, a lower alkyl group, a lower alkoxy group, an amino group, a nitro group, a lower haloalkyl group, a lower haloalkoxy group, and a cyano group.

The compounds represented by formula (I) can be prepared, for example, by reacting a benzopyran compound represented by formula (II):

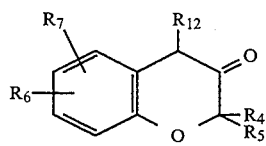

(II)

wherein $R_4$, $R_5$, $R_6$, and $R_7$ are as defined above; and $R_{12}$ represents a hydrogen atom, a lower alkyl group, or an aryl group, with a compound represented by formula (III):

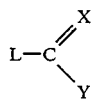

(III)

wherein X and Y are as defined above; and L represents a releasable group, e.g., a halogen atom, $-OR_{13}$, and $-S(O)_nR_{14}$, wherein $R_{13}$ and $R_{14}$ each represent a hydrogen atom, a lower alkyl group, or an aryl group, and n represents 0 or an integer of 1 or 2, in an inert solvent in the presence of a base.

The base which can be used here includes sodium hydride, a sodium alkoxide, a potassium alkoxide, an alkyl lithium, potassium carbonate, sodium carbonate, potassium hydroxide, and sodium hydroxide.

The compounds of formula (I) according to the present invention can also be prepared by reacting the compound represented by formula (II) with a compound represented by formula (IV):

$$X=C=W \qquad (IV)$$

where X is as defined above; and W represents an oxygen atom, a sulfur atom, or N-$R_{15}$, wherein $R_{15}$ represents a hydrogen atom, a hydroxyl group, a lower alkoxy group, a cyano group, a substituted or unsubstituted amino group, a substituted or unsubstituted lower alkyl group, a substituted or unsubstituted unsaturated lower alkyl group, a substituted or unsubstituted cycloalkyl group, a substituted or unsubstituted aryl group, or a substituted or unsubstituted hetero-aryl group.

The compound represented by formula (IV) includes methyl isothiocyanate.

In addition, the compounds of formula (I) can be obtained by reducing a compound represented by formula (V):

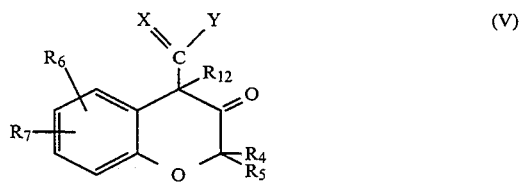

(V)

wherein X, Y, $R_4$, $R_5$, $R_6$, $R_7$, and $R_{12}$ are as defined above; or by dehydrating a compound represented by formula (VI):

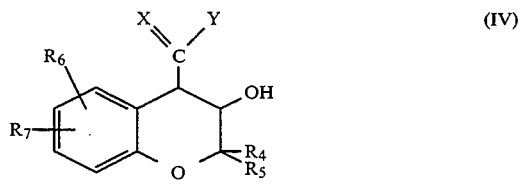

(IV)

wherein X, Y, $R_4$, $R_5$, $R_6$, and $R_7$ are as defined above, or by reducing the 3,4-double bond of the compound obtained by the dehydration.

The reduction can be carried out by reacting with a reducing agent, such as metal borohydrides or hydrides, e.g., $NaBH_4$, $KBH_4$, $LiBH_4$, $NaBH_3CN$, and $LiAlH_4$, in an inert solvent or by catalytic reduction using palladium-on-carbon, Raney nickel, etc.

The dehydration can be carried out in an inert solvent in the presence of an acid, e.g., p-toluenesulfonic acid and hydrochloric acid, or in the copresence of a base and an acid halide, e.g., p-toluenesulfonyl chloride and acetyl chloride, or an acid anhydride, e.g., acetic anhydride. Usable bases include organic bases, e.g., pyridine and triethylamine; sodium hydride, a sodium alkoxide, a potassium alkoxide, an alkyl lithium, potassium carbonate, sodium carbonate, potassium hydroxide, and sodium hydroxide.

More specifically, the compounds (I) of the present invention can be synthesized in accordance with the processes described in Examples hereinafter given.

Examples of the compounds (I) of the present invention include those listed in Table 1 below.

TABLE 1

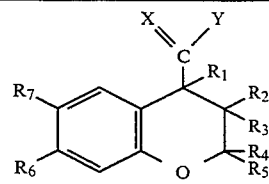

| Compound No. (Example No.) | $R_1$ | $R_2$ | $R_3$ | $R_4$ | $R_5$ | $R_6$ | $R_7$ | X | Y |
|---|---|---|---|---|---|---|---|---|---|
| 1 | — (single bond) | | OH | Me | Me | H | CN | S | MeNH |

TABLE 1-continued

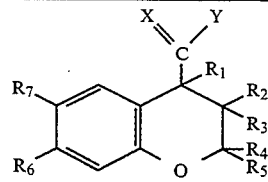

| Compound No. (Example No.) | R₁ | R₂ | R₃ | R₄ | R₅ | R₆ | R₇ | X | Y |
|---|---|---|---|---|---|---|---|---|---|
| 2 | H | H | OH | Me | Me | H | CN | S | MeNH |
| 3 | — (single bond) | | H | Me | Me | H | CN | S | MeNH |
| 4 | — (single bond) | | OH | Me | Me | H | CN | S | MeS |
| 5 | — (single bond) | | OH | Me | Me | H | CN | S | PhNH |
| 6 | — (single bond) | | OH | Me | Me | H | CN | O | PhNH |
| 7 | — (single bond) | | H | Me | Et | H | CN | S | MeNH |
| 8 | — (single bond) | | H | Me | Me | H | NO₂ | S | MeNH |
| 9 | — (single bond) | | H | Me | Me | H | CN | S | EtNH |
| 10 | — (single bond) | | H | Me | Me | H | NO₂ | O | MeNH |
| 11 | — (single bond) | | H | Me | Me | H | NO₂ | NCN | Me₂N |
| 12 | — (single bond) | | H | Me | Me | H | NO₂ | NCN | MeNH |
| 13 | — (single bond) | | H | Me | Me | H | NO₂ | O | CF₃CH₂NH |
| 14 | — (single bond) | | H | Me | Me | H | NO₂ | NCN | 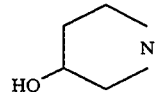 |
| 15 | — (single bond) | | H | Me | Me | H | CF₃ | O | MeNH |
| 16 | — (single bond) | | H | Et | Me | H | CN | O | MeNH |
| 17 | — (single bond) | | H | Me | Me | H | NO₂ | O | EtMeN |
| 18 | — (single bond) | | H | Me | Me | H | NO₂ | O | EtO |
| 19 | — (single bond) | | H | Me | Me | H | NO₂ | NCN | EtO |
| 20 | — (single bond) | | H | Me | Me | H | NO₂ | NCN | NH₂ |
| 21 | — (single bond) | | H | Me | Me | H | NO₂ | NCN | 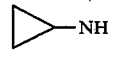 |
| 22 | H | H | H | Me | Me | H | NO₂ | O | MeNH |
| 23 | H | H | H | Me | Me | H | NO₂ | O | Me₂N |
| 24 | H | H | H | Me | Me | H | NO₂ | S | Me₂N |
| 25 | H | H | H | Me | Me | H | NO₂ | NCN | Me₂N |
| 26 | — (single bond) | | H | Me | Me | H | NO₂ | HON | Me₂N |
| 27 | — (single bond) | | H | Me | Me | H | NO₂ | NH₂SO₂N | Me₂N |
| 28 | — (single bond) | | H | Me | Me | H | NO₂ | NH₂CON | Me₂N |
| 29 | — (single bond) | | OH | Me | Me | H | NO₂ | O | NH₂ |
| 30 | — (single bond) | | H | Me | Me | H | NO₂ | O | OH |
| 31 | — (single bond) | | H | Me | Me | =N—O—N= | | O | NH₂ |
| 32 | — (single bond) | | H | Me | Me | =N—O—N= | | O | OH |
| 33 | — (single bond) | | H | Me | Me | H | AcNH | O | MeNH |
| 34 | — (single bond) | | H | Me | Me | NO₂ | AcNH | O | MeNH |
| 35 | — (single bond) | | H | Me | Me | NO₂ | NH₂ | O | MeNH |
| 36 | — (single bond) | | H | —(CH₂)₃— | | H | NO₂ | NCN | Me₂N |
| 37 | — (single bond) | | H | —(CH₂)₅— | | H | NO₂ | NCN | MeNH |

As is apparent from Text Examples hereinafter described, the compounds (I) of the present invention exhibit excellent K⁺ channel activating activity. Hence, they are useful as an active ingredient of K⁺ channel activators, such as smooth muscle relaxants, i.e., agents for treating hypertension, asthma, angina, and urinary incontinence. The dose of the compound (I) usually ranges from about 0.0001 to 1 mg/kg/day, and preferably from 0.001 to 0.1 mg/kg/day, though varying depending on the kind and severity of the disease. The administration route is appropriately selected from oral administration, non-oral administration, topical administration, and so on according to the necessity. Carriers for the K⁺ channel activators include those commonly employed as carriers.

Among the compounds (I), those having a nitro group at the 6-position, such as compounds represented by formula (VII):

$$\text{(VII)}$$

wherein X, R₄, R₅, R₈, and R₉ are as defined above, exhibit excellent K⁺ channel activating activity (refer to Test Example). In particular, those wherein either one of R₈ and R₉ is a hydrogen atom possess great activity.

Preparation of the compounds according to the present invention will hereinafter be explained in greater detail with reference to Examples; but it should be understood that the present invention is not deemed to be limited thereto.

EXAMPLE 1

N-Methyl-6-cyano-3-hydroxy-2,2-dimethyl-2H-1-benzopyran-4-carbothioamide

To a mixture of 1.5 g of 6-cyano-3,4-dihydro-2,2-dimethyl-2H-1-benzopyran-3-one, 0.6 g of methyl isothio-cyanate, and 15 ml of dried N,N-dimethylformamide was added 0.93 g of potassium t-butoxide with stirring under ice-cooling, followed by stirring for 4 hours under ice-cooling. Ice-water was added to the reaction mixture, and the mixture was made acidic with acetic acid and then extracted with diethyl ether. The ether layer was washed with water and dried over sodium sulfate. The ether layer was removed by distillation, and the residue was recrystallized from ethanol to yield 1.4 g of N-methyl-6-cyano-3-hydroxy-2,2-dimethyl-2H-1-benzopyran-4-carbothioamide represented by formula shown below.

Melting point: 186°–187° C.

NMR (CDCl$_3$): 1.5 (6H, s), 3.3 (3H, d), 7.0 (1H, d), 7.4 (1H, dd), 7.5 (1H, d), 7.6 (1H, br. s), 13.5 (1H, s)

MS: 274 (M+)

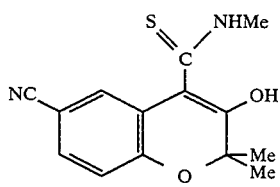

EXAMPLE 2

Cis-N-methyl-6-cyano-3,4-dihydro-3-hydroxy-2,2-dimethyl-2H-1-benzopyran-4-carbothioamide and Trans-N-methyl-6-cyano-3,4-dihydro-3-hydroxy-2,2-dimethyl-2H-1-benzopyran-4-carbothioamide To a mixture of 1.4 g of N-methyl-6-cyano-3-hydroxy-2,2-dimethyl-2H-1-benzopyran-4-carbothioamide, 15 ml of tetrahydrofuran, and 15 ml of methanol was added 0.23 g of sodium borohydride (NaBH$_4$) at $-10°$ C. with stirring, followed by stirring at $-10°$ C. for 2 hours and then at room temperature for 2 hours. The reaction mixture was distilled under reduced pressure, ice-water added to the residue, and the mixture made acidic with acetic acid and extracted with diethyl ether and ethyl acetate. The organic layer combined was dried over Na$_2$SO$_4$, followed by distillation. The residue was subjected to silica gel column chromatography (developing solution: CH$_2$Cl$_2$:AcOEt=2:1). From the first fraction was obtained 0.1 g of cis-N-methyl-6-cyano-3,4-dihydro-3-hydroxy-2,2-dimethyl-2H-1-benzopyran-4-carbothioamide represented by formula shown below.

Melting point: 170°–173° C.

NMR (CDCl$_3$): 1.3 (3H, s), 1.5 (3H, s), 3.25 (3H, d), 4.1 (1H, d), 4.5 (1H, d), 6.9 (1H, d), 7.4 (2H), 8.4 (1H, br. s)

MS: 276 (M+)

From the next fraction was then recovered 0.1 g of trans-N-methyl-6-cyano-3,4-dihydro-3-hydroxy-2,2-dimethyl-2H-1-benzopyran-4-carbothioamide represented by formula shown below.

Melting point: 213°–214° C.

NMR (CDCl$_3$): 1.2 (3H, s), 1.5 (3H, s), 3.25 (3H, d), 3.5 (1H, br. s), 4.0 (1H, d), 4.25 (1H, d), 6.9 (1H, d), 7.4 (2H), 8.3 (1H, br. s)

MS: 276 (M+)

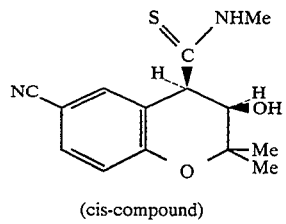

(cis-compound)

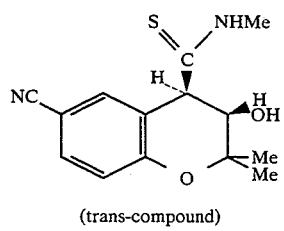

(trans-compound)

EXAMPLE 3

N-Methyl-6-cyano-2,2-dimethyl-2H-1-benzopyran-4-carbothioamide

A mixture of 0.44 g of N-methyl-6-cyano-3,4-dihydro-3-hydroxy-2,2-dimethyl-2H-1-benzopyran-4-carbothioamide, 0.07 g of p-toluenesulfonic acid monohydrate, and 30 ml of toluene was heated at reflux for 10 hours. The solvent was removed by distillation, and the residue was purified by silica gel column chromatography (developing solution: CH$_2$Cl$_2$) to obtain 0.18 g of-N-methyl-6-cyano-2,2-dimethyl-2H-1-benzopyran-4-carbothioamide represented by formula shown below.

Melting point: 139°–141° C.

NMR (CDCl$_3$): 1.5 (6H, s), 3.25 (3H, d), 5.8 (1H, s), 6.8 (1H, d), 7.4 (1H, dd), 7.7 (1H, d), 7.8 (1H, br. s)

MS: 258 (M+)

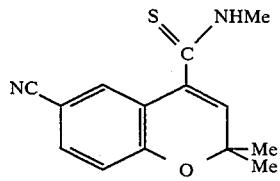

EXAMPLE 4

6-Cyano-3-hydroxy-2,2-dimethyl-2H-1-benzopyran-4-dithiocarboxylic Acid Methyl Ester To a mixture of 2.0 g of 6-cyano-3,4-dihydro-2,2-dimethyl-2H-1-benzopyran-3-one, 2.3 g of carbon disulfide, and 20 ml of dried N,N-dimethylformamide was added 1.3 g of potassium t-butoxide while stirring and ice-cooling. After stirring for 30 minutes, a mixture of 1.56 g of methyl iodide and 8 ml of dried N,N-dimethylformamide was added thereto dropwise, followed by stirring for 1 hour under cooling with ice. Ice-water was added thereto, and the reaction mixture was extracted with diethyl ether. The ether layer was washed with water and dried over sodium sulfate. The ether layer was removed by distillation, and the residue was purified by silica gel column chromatography (developing solution: CH₂Cl₂) to obtain 1.2 g of 6-cyano-3-hydroxy-2,2-dimethyl-2H-1-benzopyran-4-dithiocarboxylic acid methyl ester as a yellow oily substance.

NMR (CDCl₃): 1.5 (6H, s), 2.7 (3H, s), 7.0 (1H, d), 7.45 (1H, dd), 8.15 (1H, d), 14.65 (1H, s)

MS: 291 (M+)

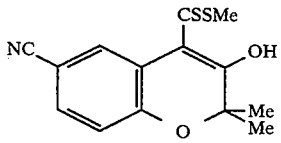

EXAMPLE 5

N-Phenyl-6-cyano-3-hydroxy-2,2-dimethyl-2H-1-benzopyran-4-carbothioamide

To a mixture of 0.5 g of 6-cyano-3,4-dihydro-2,2-dimethyl-2H-1-benzopyran-3-one, 0.37 g of phenyl isothio-cyanate, and 5 ml of dried N,N-dimethylformamide was added 0.31 g of potassium t-butoxide with under ice-cooling, followed by stirring for 5 hours under ice-cooling. Ice-water was added thereto, and the mixture was made acidic with acetic acid and extracted with diethyl ether. The extract was washed with water and dried over sodium sulfate, and the ether layer was removed by distillation. The residue was purified by silica gel column chromatography (developing solution: CH₂Cl₂) to obtain 0.4 g of N-phenyl-6- cyano-3-hydroxy-2,2-dimethyl-2H-1-benzopyran-4-carbothioamide represented by formula shown below.

Melting point: 300° C. or higher (softened at around 140° C. and then solidified)

NMR (CDCl₃): 1.5 (6H, s), 7.0 (1H, d), 7.25–7.65 (7H), 8.75 (1H, br. s), 13.55 (1H, br. s)

MS: 336 (M+)

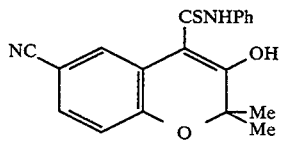

EXAMPLE 6

N-Phenyl-6-cyano-3-hydroxy-2,2-dimethyl-2H-1-benzopyran-4-carboxamide

To a mixture of 0.5 g of 6-cyano-3,4-dihydro-2,2-dimethyl-2H-1-benzopyran-3-one, 0.39 g of potassium t-butoxide, and 5 ml of dried N,N-dimethylformamide was added dropwise a mixture of 0.42 g of phenyl isocyanate and 1.5 ml of dried N,N-dimethylformamide while stirring under cooling with ice. After stirring for 4 hours under ice-cooling, ice-water was added thereto, and the mixture was made acidic with acetic acid and extracted with diethyl ether. The ether layer was washed with water and dried over sodium sulfate. Diethyl ether was removed by distillation, and the residue was purified by silica gel column chromatography (developing solution: CH₂Cl₂) to obtain 0.17 g of N-phenyl-6-cyano-3-hydroxy-2,2-dimethyl-2H-1-benzopyran-4-carboxamide represented by formula shown below.

Melting point: 167°–170° C.

NMR (CDCl₃): 1.5 (6H, s), 7.05 (1H, d), 7.25–7.75 (8H), 14.1 (1H, s)

MS: 320 (M+)

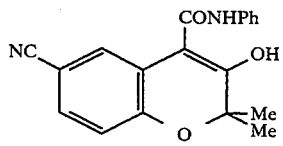

EXAMPLE 7

N,2-Dimethyl-6-cyano-2-ethyl-2H-1-benzopyran-4-carbothioamide

To a mixture of 0.8 g of N,2-dimethyl-6-cyano-2-ethyl-3-hydroxy-2H-1-benzopyran-4-carbothioamide and 20 ml of methanol was added 0.24 g of sodium borohydride (NaBH₄) while stirring under ice-cooling, followed by stirring at room temperature for 2 hours. The reaction mixture was distilled under reduced pressure, and water was added to the residue. The residue was extracted with diethyl ether, and the organic layer was washed with water and dried. The solvent was removed by distillation to obtain 0.43 g of N,2-dimethyl-6-cyano-3,4-dihydro-2-ethyl-3-hydroxy-2H-1-benzopyran-4-carbothioamide. The resulting product were added 0.1 g of p-toluenesulfonic acid monohydrate and 30 ml of toluene, followed by heating at reflux for 3 hours. The solvent was removed by distillation, and the residue was purified by silica gel column chromatography (developing solution: CH₂Cl₂) to obtain 0.2 g of N,2-dimethyl-6-cyano-2-ethyl-2H-1-benzopyran-4-carbothioamide represented by formula shown below.

Melting point: 139°–141° C.

NMR (CDCl₃): 1.0 (3H, t), 1.45 (3H, s), 1.75 (2H, m), 3.3 (3H, d), 5.8 (1H, s), 6.85 (1H, d), 7.4 (1H, dd), 7.7 (1H, d), 7.8 (1H, Br. s)

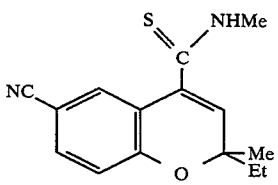

EXAMPLE 8

N,2,2-Trimethyl-6-nitro-2H-1-benzopyran-4-carbothioamide

A mixture of 7.0 g of N,2,2-trimethyl-3,4-dihydro-3-hydroxy-6-nitro-2H-1-benzopyran-4-carbothioamide, 3.0 g of p-toluenesulfonic acid monohydrate, and 300 ml of toluene was heated at reflux for 1 hour. The solvent was removed from the reaction mixture by distillation, and the residue was purified by silica gel column chromatography (developing solution: CH₂Cl₂). Recrystallization from a mixed solvent of CH₂Cl₂, diethyl ether, and hexane gave 3.25 g of N,2,2-trimethyl-6-nitro-2H-1-benzopyran-4-carbothioamide represented by formula shown below.

Melting point: 147°–148° C.

NMR (CDCl₃): 1.5 (6H, s), 3.3 (3H, d), 5.9 (1H, s), 6.85 (1H, d), 7.9 (1H, br. s), 8.0 (1H, dd), 8.3 (1H, d)

MS: 278 (M+)

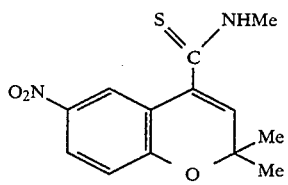

EXAMPLE 9

N-Ethyl-6-cyano-2,2-dimethyl-2H-1-benzopyran-4-carbothioamide

A mixture of 0.14 g of N-ethyl-6-cyano-2,2-dimethyl-2H-1-benzopyran-4-carbamide, 3.45 g of Lawesson's reagent, and 10 ml of benzene was refluxed for 1 hour. Any insoluble matter was collected by filtration with suction and washed with methylene chloride. The mother liquor and the washing were combined, and the solvent was removed therefrom by distillation. The residue was purified by silica gel column chromatography (developing solution: $CH_2Cl_2$) to obtain 0.12 g of N-ethyl-6-cyano-2,2-dimethyl-2H-1-benzopyran-4-carbothioamide represented by formula shown below.

Melting point: 151°–153° C.

NMR ($CDCl_3$): 1.33 (3H, t), 1.49 (6H, s), 3.56–4.10 (2H, m), 5.81 (1H, s), 6.85 (1H, d), 7.40 (1H, dd), 7.75 (1H, d), 7.82 (1H, br. s)

MS: 272 (M+)

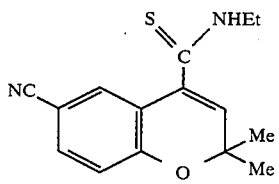

EXAMPLE 10

N-Methyl-6-nitro-2,2-dimethyl-2H-1-benzopyran-4-carboxamide

1) To a mixture of 3.2 g of 6-nitro-3,4-dihydro-2,2-dimethyl-2H-1-benzopyran-3-one, 1.2 g of methyl isothiocyanate, and 40 ml of dried N,N-dimethylformamide was added 1.9 g of potassium t-butoxide while stirring under cooling with ice. The mixture was stirred for 3 hours under ice-cooling and then allowed to stand for 12 hours. Ice-water was added thereto, and the mixture was made acidic with hydrochloric acid and then extracted with methylene chloride. The organic layer was re-extracted with 2N NaOH. The aqueous layer was made acidic with hydrochloric acid and re-extracted with methylene chloride. The organic layer was dried over magnesium sulfate and concentrated under reduced pressure. The residue was subjected to silica gel column chromatography (developing solution: n-hexane:ethyl acetate =10:1) and recrystallized from a mixed solvent of methylene chloride and n-hexane to obtain 2.33 g of N-methyl-6-nitro-3-hydroxy-2,2-dimethyl-2H-1-benzopyran-4-carbothioamide.

Melting point: 148°–149° C.

NMR ($CDCl_3$): 1.5 (6H, s), 3.25 (3H, d), 6.9 (1H, d), 7.85 (1H, dd), 8.0 (1H, d), 7.4–8.2 (1H, br), 13.5 (1H, s)

MS: 294 (M+)

2) To a mixture of 2.08 g of N-methyl-6-nitro-3-hydroxy-2,2-dimethyl-2H-1-benzopyran-4-carbothioamide and 50 ml of methanol was added 1.33 g of sodium borohydride at −10° C. while stirring. The mixture was stirred for 24 hours while slowly raising the temperature from −10° C. up to room temperature, followed by concentration under reduced pressure. Water was added to the residue, and the mixture was extracted with methylene chloride. The organic layer was washed with a saturated sodium chloride aqueous solution, dried over magnesium sulfate, and concentrated under reduced pressure. The residue was recrystallized from a mixed solvent of methylene chloride and n-hexane to obtain 0.6 g of N-methyl-6-nitro-3,4-dihydro-3-hydroxy-2,2-dimethyl-2H-1-benzopyran-4-carbothioamide.

Melting point: 203°–207° C.

NMR ($CDCl_3$-$CF_3COOD$): 1.25 (3H, s), 1.55 (3H, s), 3.3 (3H, s), 4.1 (1H, d), 4.35 (1H, d), 6.9(1H, d), 7.9 (1H, d), 8.1 (1H, dd)

MS: 296 (M+)

3) A mixture of 0.42 g of N-methyl-6-nitro-3,4-dihydro-3-hydroxy-2,2-dimethyl-2H-1-benzopyran-4-carbothioamide, 0.58 g of p-toluenesulfonyl chloride, and 30 ml of pyridine was heated under reflux for 3 hours. The reaction mixture was concentrated, and 2N hydrochloric acid was added to the residue. The mixture was extracted with dichloromethane, and the extract was dried over magnesium sulfate. The residue was purified by silica gel column chromatography ($CH_2Cl_2$) and then recrystallized from ethyl acetate to obtain 0.25 g of N-methyl-6-nitro-2,2-dimethyl-2H-1-benzopyran-4-carboxamide represented by formula shown below.

Melting point: 166°–168° C.

NMR ($CDCl_3$): 1.5 (6H, s), 2.95 (3H, d), 6.0 (1H, s), 6.8 (1H, d), 8.0 (1H, dd), 8.45 (1H, d), 5.6–6.4 (1H, m)

MS: 262 (M+)

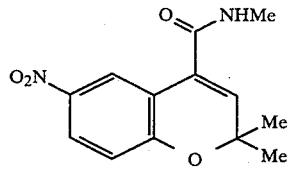

EXAMPLE 11

$N^2$-Cyano-$N^1$,$N^1$-dimethyl-6-nitro-2,2-dimethyl-2H-1-benzopyran-4-carboxamidine To a mixture of 5.25 g of N-methyl-6-nitro-2,2-dimethyl-2H-1-benzopyran-4-carboxamide obtained in the same manner as in Example 10-(3), 14.2 g of methyl iodide, and 50 ml of tetrahydrofuran was added 0.88 g of sodium hydride with stirring, followed by heating under reflux for 3 hours. Water was added to the reaction mixture, followed by extraction with methylene chloride. The organic layer was dried over magnesium sulfate and concentrated under reduced pressure. To the residue were added 4.26 g of Lawesson's reagent and 20 ml of toluene, and the mixture was heated at reflux for 1.5 hours. The reaction mixture was concentrated under reduced pressure, and the residue was subjected to silica gel chromatography (developing solution: methylene chloride) and then recrystallized from a mixed solvent of ethyl acetate and n-hexane to yield 4.86 g of N,N-dimethyl-6-nitro-2,2-dimethyl-2H-1-benzopyran-4-carbothioamide.

Melting point: 139°–141° C.

NMR (CDCl₃): 1.5 (6H, s), 3.2 (3H, s), 3.6 (3H, s), 5.65 (1H, s), 6.85 (1H, d), 7.85 (1H, d), 8.05 (1H, dd)

2) To a mixture of 2.93 g of N,N-dimethyl-6-nitro-2,2-dimethyl-2H-1-benzopyran-4-carbothioamide, 4.11 g of methyl iodide, and 30 ml of tetrahydrofuran was heated at reflux for 1 hour. When the inner temperature dropped to room temperature, 1.34 g of cyanamide and 0.44 g of sodium hydride were added thereto, followed by heating under reflux for 1 hour. The reaction mixture was concentrated under reduced pressure. Methylene chloride was added to the residue, and any insoluble matter was removed by filtration. The filtrate was concentrated under reduced pressure, and the residue was subjected to silica gel column chromatography (developing solution: mixture of n-hexane and ethyl acetate) and then recrystallized from a mixed solvent of ethyl acetate and n-hexane to obtain 2.57 g of $N^2$-cyano-$N^1,N^1$-dimethyl-6-nitro-2,2-dimethyl-2H-1-benzopyran-4-carboxamidine.

Melting point: 209°–211° C.

NMR (CDCl₃): 1.6 (6H, s), 3.0 (3H, s), 3.25 (3H, s), 5.95 (1H, s), 6.95 (1H, d), 7.7 (1H, d), 8.1 (1H, dd)

MS: 300 (M⁺) IR (KBr): 2172 cm⁻¹ (C≡N)

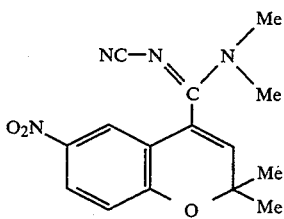

EXAMPLE 12

N-Cyano-N'-methyl-6-nitro-2,2-dimethyl-2H-1-benzopyran-4-carboxamidine

1) A mixture of 5.26 g of N-methyl-6-nitro-2,2-dimethyl-2H-1-benzopyran-4-carboxamide prepared in accordance with Example 10-(3), 4.26 g of Lawesson's reagent, and 20 ml of benzene was heated at reflux for 1.5 hours. The reaction mixture was concentrated under reduced pressure, and the residue was subjected to silica gel column chromato- graphy (developing solution: methylene chloride) and then recrystallized from a mixture of ethyl acetate and n-hexane to obtain 4.84 g of N-methyl-6-nitro-2,2-dimethyl-2H-1-benzopyran-4-carbothioamide.

Melting point: 147°–148° C.

2) A mixture of 0.56 g of N-methyl-6-nitro-2,2-dimethyl-2H-1-benzopyran-4-carbothioamide, 0.39 g of p-toluenesulfonyl chloride, 0.21 g of triethylamine, and 3 ml of acetonitrile was heated at reflux for 30 minutes. The solvent was removed by distillation, and to the residue were added 0.27 g of cyanamide, 0.17 g of sodium hydride, and 4 ml of ethanol, followed by heating under reflux for 30 minutes. Concentrated hydrochloric acid and water were added to the reaction mixture, and the mixture was extracted with methylene chloride. The organic layer was washed successively with a 2N potassium carbonate aqueous solution and a saturated sodium chloride aqueous solution and dried over magnesium sulfate. The solvent was removed by distillation, and the residue was subjected to silica gel column chromatography (developing solution: n-hexane:ethyl acetate=1:1) and then recrystallized from a mixture of ethyl acetate and diethyl ether to obtain 50 mg of the titled compound.

Melting point: 240°–243° C.

NMR (CDCl₃): 1.6 (6H, s), 3.1 (3H, d), 5.9–6.2 (1H, bs), 6.1 (1H, s), 6.9 (1H, d), 7.85 (1H, d), 8.1 (1H, dd)

MS: 286 (M⁺) IR (KBr): 2180 cm⁻¹ (C≡N)

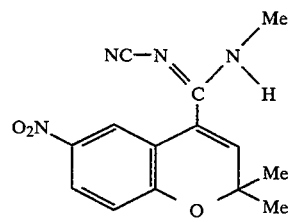

EXAMPLE 13

N-(2',2',2'-Trifluoroethyl)-6-nitro-2,2-dimethyl-2H-1-benzopyran-4-carboxamide

A mixture of 1.00 g of 6-nitro-2,2-dimethyl-2H-1-benzopyran-4-carboxylic acid, 0.44 g of 2,2,2-trifluoroethylamine, 0.97 g of 2,2'-dipyridyl disulfide, 1.16 g of triphenylphosphine, and 20 ml of dichloromethane was stirred at room temperature for 3 hours. The solvent was removed therefrom by distillation, and the residue was purified by silica gel column chromatography (developing solution; AcOEt:n-hexane=1:1) and then recrystallized from a mixture of n-hexane and ethyl acetate to obtain 0.98 g of N (2',2',2'-trifluoroethyl)-6-nitro-2,2-dimethyl-2H-1-benzopyran-4-carboxamide represented by formula shown below.

Melting point: 178°–180° C.

NMR (CDCl₃): 1.5 (6H, s) , 3.7–4.4 (2H, m), 6.1 (1H, s), 6.85 (1H, d) , 8.05 (1H, dd), 8.4 (1H, d)

MS: 330 (M⁺)

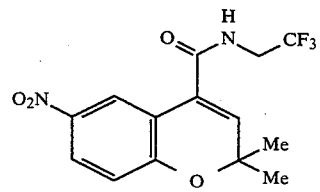

EXAMPLE 14

N-(N'-Cyano-6-nitro-2,2-dimethyl-2H-1-benzopyran-4-yliminoyl)-pyrrolidin-3-ol

A mixture of 0.11 g of N-(N'-cyano-6-nitro-2,2-dimethyl-2H-1-benzopyran-4-yliminoyl)-3-t-butyl-dimethyl-silyloxypyrrolidine, 0.5 ml of a 1 mol/l solution of tetra-n-butylammonium fluoride in tetrahydrofuran, and 5 ml of tetrahydrofuran was stirred for 1 hour under cooling with ice. The solvent was removed by distillation, and the residue was purified by silica gel column chromatography (AcOEt:n-hexane=1:5) and recrystallization from a mixture of n-hexane and ethyl acetate to obtain 28 mg of N-(N'-cyano-6-nitro-2,2-dimethyl-2H-1-benzopyran-4-yliminoyl)-pyrrolidin-3-ol represented by formula shown below.

Melting point: 199°–200 ° C.

NMR (CDCl₃): 1.6 (6H, s), 1.7–4.8 (8H, m), 6.0 (1H, s), 6.9 (1H, d), 7.55–7.8 (1H, m) 8.05 (1H, dd)

MS: 342 (M⁺)

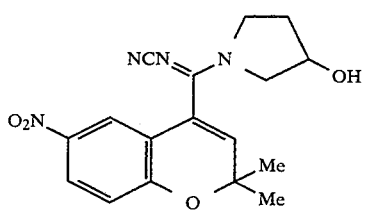

EXAMPLE 15

N-Methyl-6-trifluoromethyl-2,2-dimethyl-2H-1-benzopyran-4-carboxamide

A mixture of 0.17 g of N-methyl-3,4-dihydro-3-hydroxy-6-trifluoromethyl-2,2-dimethyl-2H-1-benzopyran-4-carbothioamide, 0.21 g of p-toluenesulfonyl chloride, and 10 ml of pyridine was heated at reflux for 4 hours. To the reaction mixture was added 2N hydrochloric acid, and the mixture was extracted with dichloromethane. The extract was dried over magnesium sulfate. The residue was purified by silica gel column chromatography (CH$_2$Cl$_2$:methanol=100:1) and then recrystallized from a mixture of diethyl ether and n-hexane to obtain 44 mg of N-methyl-6-trifluoromethyl-2,2-dimethyl-2H-1-benzopyran-4-carboxamide represented by formula shown below.

Melting point: 146°–150° C.

NMR (CDCl$_3$): 1.4 (6H, s), 2.85 (3H, d), 5.95 (1H, s), 6.1–6.7 (1H, m), 6.8 (1H, d), 6.35 (1H, dd), 7.75 (1H, d)

MS: 285 (M+)

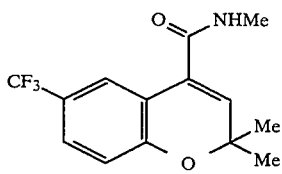

EXAMPLE 16

N-Methyl-6-cyano-2-ethyl-2-methyl-2H-1-benzopyran-4-carbamide

A mixture of 70 mg of N-methyl-6-cyano-2-ethyl-2-methyl-2H-1-benzopyran-4-carbothioamide, 55 mg of p-toluenesulfonyl chloride, and 5 ml of pyridine was heated at reflux for 6 hours. To the reaction mixture was added 2N hydrochloric acid, and the mixture was extracted with dichloromethane. The extract was dried over magnesium sulfate, and purified by silica gel column chromatography (AcOEt:n-hexane=1:1) and recrystallized from a mixture of ethyl acetate and n-hexane to obtain 41 mg of N-methyl-6-cyano-2-ethyl-2-methyl-2H-1-benzopyran-4-carboxamide represented by formula shown below.

Melting point: 152°–154° C.

NMR (CDCl$_3$): 0.95 (3H, t), 1.4 (3H, s), 1.8 (2H, q), 2.9 (3H, d), 6.0 (1H, s), 6.2–6.7 (1H, m), 6.8 (1H, d), 7.4 (1H, dd), 7.85 (1H, d)

MS: 256 (M+)

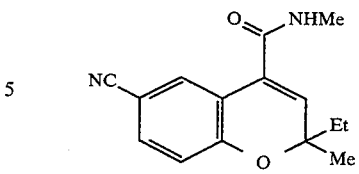

EXAMPLE 17

N-Ethyl-N-methyl-6-nitro-2,2-dimethyl-2H-1-benzopyran-4-carboxamide

A mixture of 0.53 g of N-methyl-6-nitro-2,2-dimethyl-2H-1-benzopyran-4-carboxamide, 1.60 g of ethyl iodide, 0.09 g of sodium hydride, and 10 ml of tetrahydrofuran was heated at reflux for 30 minutes. Dichloromethane was added to the reaction mixture, and any insoluble matter was removed by filtration. The filtrate was recrystallized from a mixture of diethyl ether and n-hexane to obtain 0.45 g of N-ethyl-N-methyl-6-nitro-2,2-dimethyl-2H-1-benzopyran-4-carboxamide represented by formula shown below.

Melting point: 121°–124° C.

NMR (CDCl$_3$): 0.9–1.5 (3H, m), 1.5 (6H, s), 2.8–3.8 (5H, m), 5.7 (1H, s), 6.95 (1H, d), 7.9 (1H, d), 8.1 (1H, dd)

MS: 290 (M+)

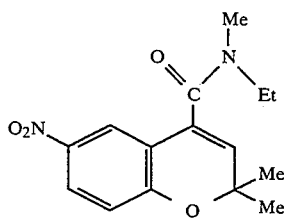

EXAMPLE 18 TO 20

N-Cyano-6-nitro-2,2-dimethyl-2H-1-benzopyran-4-carboximidic Acid Ethyl Ester,
N-Cyano-6-nitro-2,2-dimethyl-2H-1-benzopyran-4-carboxamidine, and
6-Nitro-2,2-dimethyl-2H-1-benzopyran-4-carboxylic Acid Ethyl Ester To a mixture of 1.04 g of 4-cyano-6-nitro-2,2-dimethyl-2H-1-benzopyran and 20 ml of ethyl alcohol was added hydrogen chloride with stirring and cooling with ice. After being saturated with hydrogen chloride, the mixture was further stirred at 5° C. for 6 days. The reaction mixture was concentrated, and to the residue was added a 1:1 mixture of diethyl ether and ethyl alcohol. After trituration, the crystal was collected by filtration, washed with a mixture of ethyl alcohol and diethyl ether, and dried to obtain 1.13 g of 6-nitro-2,2-dimethyl-2H-1-benzopyran-4-carboximidic acid ethyl ester hydrochloride. A mixture of 0.94 g of the resulting compound, 0.31 g of triethylamine, 0.13 g of cyanamide, and 7 ml of ethyl alcohol was stirred at room temperature for 6 hours, followed by concentration. Water was added to the residue, and the mixture was extracted with dichloromethane. The extract was washed with 2N hydrochloric acid, dried over magnesium sulfate, and subjected to silica gel column chromatography (AcOEt:n-hexane=1:1) to isolate three components having different polarity. The component of the lowest polarity was recrystallized from a mixture of diethyl ether and n-hexane to obtain 0.15 g of 6-nitro-2,2-dimethyl-2H-1-benzopyran-4-carboxylic acid ethyl ester represented by formula shown below.

Melting point: 96°–97° C.
NMR (CDCl$_3$): 1.4 (3H, t), 1.5 (6H, s), 4.35 (2H, q), 6.8 (1H, s), 6.85 (1H, d), 8.05 (1H, dd), 9.0 (1H, d)
MS: 277 (M+)

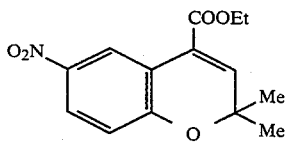

The component of the second lowest polarity was recrystallized from a mixture of ethyl acetate and n-hexane to obtain 0.14 g of N-cyano-6-nitro-2,2-dimethyl-2H-1-benzopyran-4-carboximidic acid ethyl ester represented by formula shown below.

Melting point: 91°–93° C.
NMR (CDCl$_3$): 1.5 (3H, t), 1.6 (6H, s), 4.6 (2H, q), 6.5 (1H, s), 6.85–7.1 (1H, m), 8.0–8.3 (2H, m)
MS: 301 (M+)

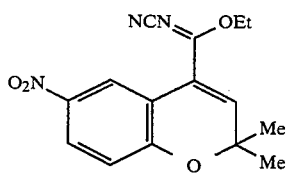

The component of the highest polarity was recrystallized from a mixture of ethyl acetate and n-hexane to obtain 0.08 g of N-cyano-6-nitro-2,2-dimethyl-2H-1-benzopyran-4-carboxamidine represented by formula shown below.

Melting point: 205°–207° C.
NMR (CDCl$_3$): 1.5 (6H, s), 5.6–6.5 (2H, m), 6.2 (1H, s), 6.9 (1H, d), 8.05 (1H, dd), 8.55 (1H, d)
MS: 272 (M+)

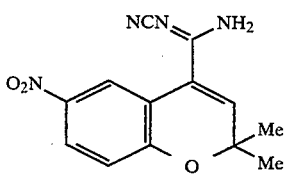

EXAMPLE 21

N-Cyano-N'-cyclopropyl-6-nitro-2,2-dimethyl-2H-1-benzopyran-4-carboxamidine

A mixture of 98 mg of N-cyano-6-nitro-2,2-dimethyl-2H-1-benzopyran-4-carboximidic acid ethyl ester, 30 mg of cyclopropylamine, and 1 ml of dichloromethane was stirred at room temperature for 1.5 hours. The reaction mixture was subjected to silica gel column chromatography (AcOEt:n-hexane=1:1) and then recrystallization from a mixture of acetone and n-hexane to obtain 30 mg of N-cyano-N'-cyclopropyl-6-nitro-2,2-dimethyl-2H-1-benzopyran -4-carboxamidine represented by formula shown below.

Melting point: 206°–207° C.
NMR (CDCl$_3$): 0.5–1.0 (4H, m), 1.5 (6H, s), 2.7–3.2 (1H, m), 5.9 (1H, s), 6.8 (1H, d), 6.9–7.4 (1H, m), 7.7 (1H, d), 8.0 (1H, dd)
MS: 312 (M+)

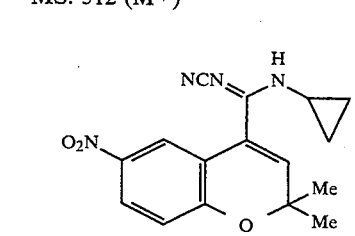

EXAMPLE 22

N-Methyl-3,4-dihydro-6-nitro-2,2-dimethyl-2H-1-benzopyran-4-carboxamide

A mixture of 0.53 g of N-methyl-6-nitro-2,2-dimethyl-2H-1-benzopyran-4-carboxamide, 0.38 g of sodium borohydride, 5 ml of tetrahydrofuran, and 5 ml of methyl alcohol was stirred at room temperature for 20 minutes. 2N Hydrochloric acid was added thereto, followed by extracting with dichloromethane. The extract was dried over magnesium sulfate and recrystallized from ethyl acetate and n-hexane to obtain 0.42 g of N-methyl-3,4-dihydro-6-nitro-2,2-dimethyl-2H-1-benzopyran-4-carboxamide represented by formula shown below.

Melting point: 161°–162° C.
NMR (CDCl$_3$): 1.3 (3H, s), 1.4 (3H, s), 1.9–2.4 (2H, m), 2.85 (3H, d), 3.7 (1H, dd), 5.7–6.3 (1H, m), 6.85 (1H, d), 7.85–8.2 (2H, m)
MS: 264 (M+)

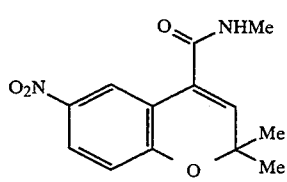

EXAMPLE 23

N,N-Dimethyl-3,4-dihydro-6-nitro-2,2-dimethyl-2H-1-benzopyran-4-carboxamide

A mixture of 2.63 g of N-methyl-6-nitro-2,2-dimethyl-2H-1-benzopyran-4-carboxamide, 1.90 g of sodium borohydride, 25 ml of tetrahydrofuran, and 25 ml of methyl alcohol was stirred at room temperature for 20 minutes. 2N Hydrochloric acid was added thereto, followed by extracting with dichloromethane. The extract was dried over magnesium sulfate. The solvent was removed by distillation, and to the residue were added 7.1 g of methyl iodide, 0.44 g of sodium hydride, and 50 ml of tetrahydrofuran, followed by heating under reflux for 30 minutes. 2N Hydrochloric acid was added thereto, and the mixture was extracted with dichloromethane. The extract was washed with a saturated sodium chloride aqueous solution and dried over magnesium sulfate. The residue was purified by silica gel column chromatography (CH$_2$Cl$_2$) and recrystallized from a mixture of ethyl acetate and n-hexane to obtain 0.49 g of N,N-methyl-3,4-dihydro-6-nitro-2,2-dimethyl-2H-1-benzopyran-4-carboxamide represented by formula shown below.

Melting point: 162°–164° C.

NMR (CDCl$_3$): 1.35 (3H, s), 1.5 (3H, s), 1.75-2.5 (2H, m), 2.1 (3H, s), 2.25 (3H, s), 4.2 (1H, dd), 6.85 (1H, d), 7.8-8.2 (2H, m)

MS: 278 (M+)

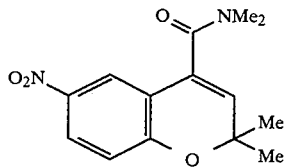

EXAMPLE 24

N,N-Dimethyl-3,4-dihydro-6-nitro-2,2 dimethyl-2H-1-benzopyran-4-carbothioamide

A mixture of 0.43 g of N,N-dimethyl-3,4-dihydro-6-nitro-2,2-dimethyl-2H-1-benzopyran-4-carboxamide, 0.33 g of Lawesson's reagent, and 2 ml of benzene was heated under reflux for 30 minutes. The reaction product was purified by silica gel column chromatography (CH$_2$Cl$_2$) and recrystallized from a mixture of ethyl acetate and n-hexane to obtain 0.33 g of N,N-dimethyl-3,4-dihydro-6-nitro-2,2-dimethyl-2H-1-benzopyran-4-carbothioamide represented by formula shown below.

Melting point: 158°-160° C.

NMR (CDCl$_3$): 1.3 (3H, s), 1.5 (3H, s), 1.8-2.7 (2H, m), 3.3 (3H, s), 3.6 (3H, s), 4.6 (1H, dd) 6.8 (1H, d), 7.75-8.2 (2H, m)

MS: 294 (M+)

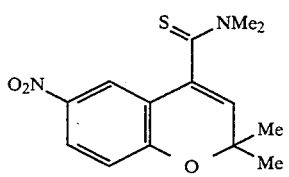

EXAMPLE 25

N-Cyano-N',N'-dimethyl-3,4-dihydro-6-nitro-2,2-dimethyl-2H-1-benzopyran-4-carboxamidine A mixture of 0.27 g of N,N-dimethyl-3,4-dihydro-6-nitro-2,2-dimethyl-2H-1-benzopyran-4-carbothioamide, 0.66 g of methyl iodide, and 2 ml of tetrahydrofuran was heated under reflux for 1 hour. To the reaction mixture were added 40 mg of sodium hydride and 44 mg of cyanamide, and refluxing was further continued for an additional period of 2 hours. Dichloromethane was added to the reaction mixture, and any insoluble matter was removed by filtration. The filtrate was purified by silica gel column chromatography (AcOEt:n-hexane=1:1) and then recrystallized from a mixture of ethyl acetate and n-hexane to obtain 90 mg of N-cyano-N',N'-dimethyl-3,4-dihydro-6-nitro-2,2-dimethyl-2H-1-benzopyran-4-carboxamidine represented by formula shown below.

Melting point: 222°-224° C.

NMR (CDCl$_3$): 1.35 (3H, s), 1.6 (3H, s), 1.8-5.5 (9H, m), 6.95 (1H, d), 7.8-8.3 (2H, m)

MS: 302 (M+)

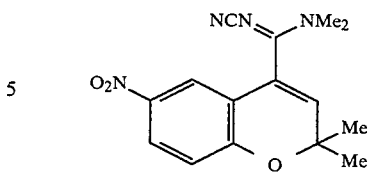

EXAMPLE 26

N-Hydroxy-N',N'-dimethyl-6-nitro-2,2-dimethyl-2H-1-benzopyran-4-carboxamidine

A mixture of 0.30 g of N,N-dimethyl-6-nitro-2,2-dimethyl-2H-1-benzopyran-4-carbothioamide, 2.5 g of methyl iodide, and 10 ml of tetrahydrofuran was heated at reflux for 30 minutes. To the reaction mixture were added 0.37 g of hydroxylamine hydrochloride and 0.15 g of trimethylamine, and refluxing was further continued for 1.5 hours. A potassium carbonate aqueous solution was added to the reaction mixture, and the mixture was extracted with dichloromethane. The extract was dried over magnesium sulfate, and purified by silica gel column chromatography (AcOEt:n-hexane=1:1) and then recrystallized from a mixture of dichloromethane and n-hexane to obtain 72 mg of N-hydroxy-N',N'-dimethyl-6-nitro-2,2-dimethyl-2H-1-benzopyran-4-carboxamidine represented by formula shown below.

NMR (CDCl$_3$): 1.55 (6H, s), 2.75 (6H, s), 5.8 (1H, s), 6.9 (1H, d), 7.4-8.2 (3H, m)

MS: 291 (M+)

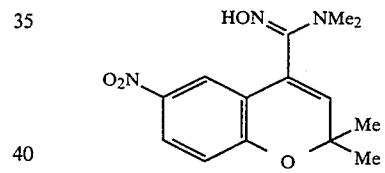

EXAMPLE 27

N-Sulfamoyl-N',N'-dimethyl-6-nitro-2,2-dimethyl-2H-1-benzopyran-4-carboxamidine

A mixture of 0.29 g of N,N-dimethyl-6-nitro-2,2-dimethyl-2H-1-benzopyran-4-carbothioamide, 0.71 g of methyl iodide, and 2 ml of tetrahydrofuran was heated at reflux for 30 minutes. To the reaction mixture were added 105 mg of sulfamide and 44 mg of sodium hydride, followed by refluxing for 5 hours. 2N Hydrochloric acid was added to the reaction mixture, and the mixture was extracted with dichloromethane. The extract was washed with a saturated sodium chloride aqueous solution, dried over magnesium sulfate, purified by silica gel column chromatography (AcOEt:n-hexane=1:1), and then recrystallized from a mixture of ethyl acetate and n-hexane to obtain 0.17 g of N-sulfamoyl-N',N'-dimethyl-6-nitro-2,2-dimethyl-2H-1-benzopyran-4-carboxamidine represented by formula shown below.

Melting point: 212°-214° C.

NMR (CDCl$_3$): 1.55 (3H, s), 1.6 (3H, s), 2.9 (3H, s), 3.2 (3H, s), 4.4-4.8 (2H, m), 5.95 (1H, s), 6.9 (1H, d), 7.7 (1H, d), 8.1 (1H, dd)

MS: 354 (M+)

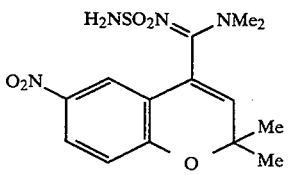

EXAMPLE 28

N-Carbamoyl-N',N'-dimethyl-6-nitro-2,2-dimethyl-2H-1-benzopyran-4-carboxamidine

To a mixture of 300 mg of N-cyano-N',N'-dimethyl-6-nitro-2,2-dimethyl-2H-1-benzopyran-4-carboxamidine, 10 ml of ethyl alcohol, and 10 ml of chloroform was added hydrogen chloride gas under cooling with ice. After being saturated with hydrogen chloride, the mixture was stirred at 6° C. for 10 days, followed by concentration. To the residue was added a saturated sodium hydrogencarbonate aqueous solution, and the mixture was extracted with dichloromethane. The extract was dried over sodium sulfate and purified by silica gel column chromatography (AcOEt:n-hexane=1:1) and then by recrystallization from a mixture of ethyl acetate and n-hexane to obtain 236 mg of N-carbamoyl-N',N'-dimethyl-6-nitro-2,2-dimethyl-2H-1-benzopyran-4-carboxamidine represented by formula shown below.

Melting point: 157°-159° C.

NMR (CDCl$_3$): 1.5 (3H, s), 1.55 (3H, s), 2.9 (3H, s), 3.15 (3H, s), 4.6-5.4 (2H, m), 5.7 (1H, s), 6.85 (1H, d), 7.8 (1H, d), 8.05 (1H, dd)

MS: 318 (M+)

EXAMPLE 29

3-Hydroxy-2,2-dimethyl-6-nitro-2H-1-benzopyran-4-carboxamide

To a mixture of 41.5 g of 3,4-dihydro-2,2-dimethyl-6-nitro-2H-1-benzopyran-3-one and 500 ml of dried N,N-dimethylformamide was slowly added 8.2 g of sodium hydride (60%) in a nitrogen stream while stirring under cooling with ice. After stirring for 50 minutes, 33.5 g of carbonyl diimidazole was added thereto and the mixture stirred for 1 hour. To the reaction mixture were added 11.2 g of ammonium chloride and 29 ml of triethylamine, followed by stirring at 5° C. for 12 hours and then at room temperature for 14 hours. Ice-water was added to the reaction mixture, and the mixture was washed with diethyl ether. The aqueous layer was made acidic with hydrochloric acid and extracted with a mixed solvent of ethyl acetate and diethyl ether. The organic layer was washed with water and dried. The solvent was removed by distillation, and the residue was purified by silica gel column chromatography (developing solution: CH$_2$Cl$_2$:MeOH=99:1) to obtain 23.2 g of 3-hydroxy-2,2-dimethyl-6-nitro-2H-1-benzopyran-4-carboxamide represented by formula shown below.

Melting point: 189°-191° C.

NMR (CDCl$_3$-CD$_3$OD): 1.50 (6H, s), 7.00 (1H, d), 7.97 (1H, dd), 8.27 (1H, d)

MS: 264 (M+)

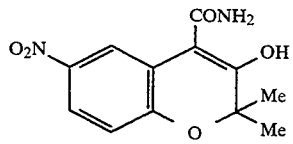

EXAMPLE 30

2,2-Dimethyl-6-nitro-2H-1-benzopyran-4-carboxylic Acid

To a mixture of 23.2 g of 3-hydroxy-2,2-dimethyl-6-nitro-2H-1-benzopyran-4-carboxamide, 16.6 g of sodium cyanoborohydride, and 200 ml of tetrahydrofuran was added 100 ml of acetic acid with stirring and ice-cooling, followed by stirring for 3 hours under ice-cooling and then at room temperature for 18 hours. To the reaction mixture were further added 5.6 g of sodium cyanoborohydride and 50 ml of methanol, followed by stirring at room temperature for 40 hours. The reaction mixture was distilled under reduced pressure, water was added to the residue, and the mixture was extracted with a mixed solvent of ethyl acetate and diethyl ether. The organic layer was washed with water and dried, and the solvent was removed by distillation to recover 24 g of 3,4-dihydro-3-hydroxy-2,2-dimethyl-6-nitro-2H-1-benzopyran-4-carboxamide. To the resulting compound were added 51.5 g of p-toluenesulfonyl chloride and 400 ml of pyridine, followed by refluxing for 3 hours. The solvent was removed from the reaction mixture by distillation. Ice-water was added to the residue, and the mixture was made acidic with hydrochloric acid. The thus precipitated crystal was collected by filtration, washed with water, and dried. The crystal was further purified by silica gel column chromatography (developing solution: CH$_2$Cl$_2$:hexane=7:3) to give 17.9 g of 4-cyano-2,2-dimethyl-6-nitro-2H-1-benzopyran represented by formula shown below.

Melting point: 162°-164° C.

NMR (CDCl$_3$): 1.58 (6H, s), 6.51 (1H, s), 6.94 (1H, d), 8.15 (1H, dd), 8.23 (1H, d)

MS: 230 (M+)

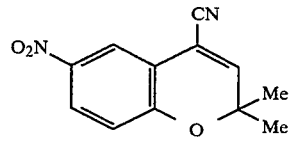

A mixture of 13.0 g of 4-cyano-2,2-dimethyl-6-nitro-2H-1-benzopyran, 400 ml of acetic acid, 200 ml of water, and 100 ml of concentrated sulfuric acid was heated at reflux for 1.5 hours. After adding 100 ml of concentrated sulfuric acid, the refluxing was further continued for an additional period of 1 hour. The reaction mixture was poured into ice-water. The thus precipitated crystal was washed with water, dried, and recrystallized from a mixed solvent of acetonitrile and water to obtain 11.9 g of 2,2-dimethyl-6-nitro-2H-1-benzopyran-4-carboxylic acid represented by formula shown below.

Melting point: 203°–204° C. NMR (CDCl₃-CD₃OD)): 1.50 (6H, s), 6.80 (1H, s), 6.85 (1H, d), 8.03 (1H, dd), 8.99 (1H, d)

MS: 249 (M+)

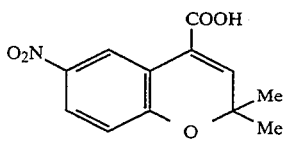

EXAMPLE 31

6,6-Dimethyl-6H-pyrano[2,3-f]benzo-2,1,3-oxadiazole-8-carboxamide

To a mixture of 3.9 g of 7,8-dihydro-6,6-dimethyl-7,8-epoxy-6H-pyrano[2,3-f]benzo-2,1,3-oxadiazole and 80 ml of toluene was added dropwise 90 ml of a 1.0M solution of diethyl-aluminum cyanide in toluene with stirring under ice-cooling, followed by stirring at room temperature for 2 hours. The reaction mixture was poured into ice-water, and 2N NaOH was added thereto. The mixture was extracted with methylene chloride, and the organic layer was washed with water and dried. The solvent was removed by distillation, and the residue was purified by silica gel column chromatography (developing solution: CH₂Cl₂) to obtain 2.9 g of 8-cyano-6,6-dimethyl-6H-pyrano[2,3-f]benzo-2,1,3-oxadiazole represented by formula shown below.

Melting point: 136°–138° C.

NMR (CDCl₃): 1.55 (6H, s), 6.83 (1H, s), 7.03 (1H, s), 7.83 (1H, s)

MS: 227 (M+)

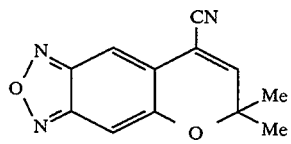

A mixture of 0.66 g of 8-cyano-6,6-dimethyl-6H-pyrano[2,3-f]benzo-2,1,3-oxadiazole and 15 ml of concentrated sulfuric acid was stirred at room temperature for 45 hours. The reaction mixture was poured into ice-water and extracted with diethyl ether. The organic layer was washed with water, dried, and distilled to remove the solvent. The residue was purified by silica gel column chromatography (developing solution: CH₂Cl₂:MeOH=99:1) and recrystallized from a mixed solvent of ethyl acetate and hexane to obtain 0.35 g of 6,6-dimethyl-6H-pyrano[2,3f]benzo-2,1,3-oxadiazole-8-carboxamide represented by formula shown below.

Melting point: 168°–169° C.

NMR (CDCl₃): 1.52 (6H, s), 6.30 (2H, br. s). 6.60 (1H, s), 7.07 (1H, s), 8.18 (1H, s)

MS: 245 (M+)

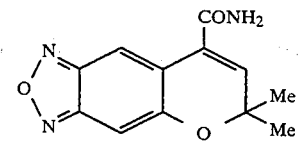

EXAMPLE 32

6,6-Dimethyl-6H-pyrano[2,3-f]benzo-2,1,3-oxadiazole-8-carboxylic Acid

In the same manner as in Example 30, except for using 1.74 g of 8-cyano-6,6-dimethyl-6H-pyrano[2,3-f]benzo-2,1,3-oxadiazole, 1.76 g of 6,6-dimethyl-6H-pyrano[2,3f]benzo-2,1,3-oxadiazole-8-carboxylic acid represented by formula shown below was obtained.

Melting point: 246°–248° C.

NMR (CDCl₃): 1.52 (6H, s), 7.07 (1H, s), 7.27 (1H, s), 8.61 (1H, s)

MS: 246 (M+)

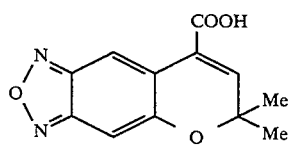

EXAMPLE 33

N,2,2-Trimethyl-6-acetylamide-2H-1-benzopyran-4-carboxamide

A mixture of 1.55 g of N,2,2-trimethyl-6-nitro-2H-1-benzopyran-4-carboxamide, 3.84 g of stannous chloride, and 30 ml of dried ethanol was heated at reflux for 4 hours. The solvent was removed by distillation, and 15 ml of acetic anhydride was added to the residue, followed by stirring at room temperature for 17 hours. The reaction mixture was distilled under reduced pressure and 2N hydrochloric acid was added to the residue. The mixture was extracted with a mixed solvent of ethyl acetale and diethyl ether, and the organic layer was washed with water and dried. The solvent was removed by distillation, and the residue was purified by silica gel column chromatography (developing solution: CH₂Cl₂:MeOH=99:1) to obtain 1.30 g of N,2,2-trimethyl-6-acetylamide-2H-1-benzopyran-4-carboxamide represented by formula shown below.

Melting point: 203°–210° C.

NMR (CDCl₃-DMSO-d₆): 1.42 (6H, s), 2.06 (3H, s), 2.85 (3H, d), 5.99 (1H, s), 6.74 (1H. br. d), 7.50 (1H, br. s), 7.52 (1H, s), 7.60 (1H, br. d), 9.43 (1H, br. s)

MS: 274 (M+)

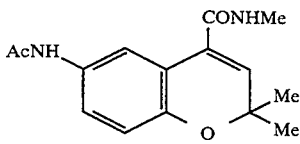

EXAMPLE 34

N,2,2-Trimethyl-6-acetylamide-7-nitro-2H-1-benzopyran-4-carboxamide

To a mixture of 1.16 g of N,2,2-trimethyl-6-acetylamide-2H-1-benzopyran-4-carboxamide and 15 ml of acetic acid was added a solution of 0.50 ml of fuming nitric acid in 2 ml of acetic acid while stirring under ice-cooling, followed by stirring at room temperature for 1 hours. Ice-water was added to the reaction mixture, and the mixture was extracted with a mixed solvent of ethyl acetate and diethyl ether. The organic layer was washed with water, dried, and distilled to remove the solvent. The residue was purified by silica gel column chromatography (developing solution: CH₂Cl₂:MeOH=99:1) to obtain 0.55 g of N,2,2-trimethyl-6-acetylamide-7-nitro-2H-1-benzopyran-4-carboxamide having formula shown below.

Melting point: 213°–215° C.

NMR (CDCl₃): 1.45 (6H, s), 2.23 (3H, s), 2.96 (3H, d), 6.25 (1H, br. s), 6.29 (1H, s), 7.59 (1H, s), 8.66 (1H, s), 9.92 (1H, br. s)

MS: 319 (M+)

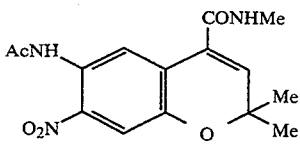

EXAMPLE 35

N,2,2-Trimethyl-6-amino-7-nitro-2H-1-benzopyran-4-carboxamide

A mixture of 0.50 g of N,2,2-trimethyl-6-acetylamide-7-nitro-2H-1-benzopyran-4-carboxamide, 15 ml of ethanol, and 2N sodium hydroxide was stirred at room temperature for 3 hours. A saturated sodium chloride aqueous solution was added to the reaction mixture, followed by extracting with diethyl ether. The organic layer was washed with a saturated sodium chloride aqueous solution, dried, and distilled to remove the solvent to obtain 0.40 g of N,2,2trimethyl-6-amino-7-nitro-2H-1-benzopyran-4-represented by formula shown below.

Melting point: 202°–205 ° C.

NMR (CDCl₃): 1.43 (6H, s), 2.93 (3H, d), 5.91 (3H, br. s), 6.20 (1H, s), 7.13 (1H, s), 7.52 (1H, s)

MS: 277 (M+)

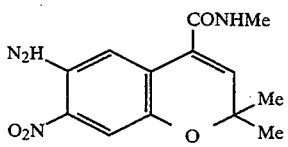

EXAMPLE 36

N-Cyano-N,N'-dimethyl-6-nitrospiro-[2H-1-benzopyran-2,1'-cyclobutane]-4-carboxamidine To a mixture of 0.08 g of N,N'-dimethyl-6-nitrospiro-[2H-1-benzopyran-2,1'-cyclobutane]-4-carbothioamide, 0.42 g of iodomethane, 0.08 g of cyanamide, and 4 ml of dried tetrahydrofuran was added 0.08 g of sodium hydride (60%) while stirring under ice-cooling. The mixture was stirred at room temperature for 12 hours and then at 40° C. for 30 minutes. Ice-water was added thereto, and the mixture was extracted with methylene chloride. The organic layer was washed with water and dried, and the solvent was removed by distillation. The residue was purified by silica gel column chromatography (developing solution: CH₂Cl₂:MeOH=99:1) and recrystallized from a mixed solvent of ethyl acetate and hexane to obtain 0.06 g of N-cyano-N,N'-dimethyl-6-nitrospiro-[2H-1-benzopyran-2,1'-cyclobutane]-4-carboxamidine represented by formula shown below.

Melting point: 185°–187° C.

NMR (CDCl₃): 1.56–2.88 (6H, m), 3.00 (3H, s), 3.24 (3H, s), 6.25 (1H, s), 6.88 (1H, d), 7.56 (1H, d), 8.01 (1H, dd)

MS: 312 (M+)

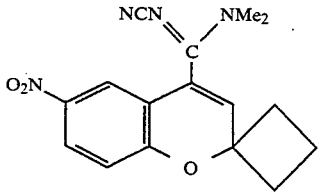

EXAMPLE 37

N-Cyano-N'-methyl-6-nitrospiro-[2H-1-benzopyran-2,1'-cyclohexane]-4-carboxamidine To a mixture of 120 mg of N-methyl-6-nitrospiro[2H-1benzopyran-2,1'-cyclohexane]-4-carbothioamide, 150 μl of iodoethane, and 3 ml of dried tetrahydrofuran was added 23 mg of sodium hydride (60%) with stirring and cooling with ice followed by refluxing for 2 hours. After cooling to room temperature, 80 mg of cyanamide and 17 mg of sodium hydride (60%) were added thereto, followed by refluxing for 4 hours. Ice-water was added thereto, and the mixture was extracted with ethyl acetate. The organic layer was washed with water and dried, and the solvent was removed by distillation. The residue was purified by silica gel column chromatography (developing solution: ethyl acetate:-hexane=2:3) recrystallized from a mixed solvent of ethyl acetate and hexane to obtain 90 mg of N-cyano-N'-methyl-6-nitrospiro[2H-1-benzopyran-2,1'-cyclohexane]-4-carboxamidine having formula shown below.

Melting point: 244°–245° C.

NMR (CDCl₃-CD₃OD): 1.40–2.20 (10H, m), 2.95 (3H, d), 5.95 (1H, s), 6.85 (1H, d), 7.75 (1H, d), 8.00 (1H, dd)

MS: 326 (M+)

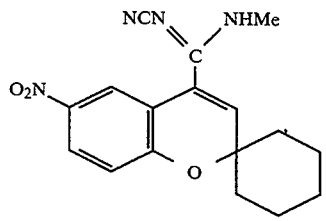

EXAMPLES 38 TO 315

Compounds shown in Table 2 below were synthesized in accordance with the procedures described in the foregoing Examples.

TABLE 2

(I)

[Structure: Chromene-type compound with substituents X=C(Y)-R1, R2, R3, R4, R5 on the ring, and R6, R7 on the benzene ring, with O in the ring]

| Compound No. | R1 | R2 | R3 | R4 | R5 | R6 | R7 | X | Y | Melting Point (°C) | MS (M+) | IR (KBr) (cm$^{-1}$) | Process of Synthesis |
|---|---|---|---|---|---|---|---|---|---|---|---|---|---|
| 38 | — | (single bond) | OH | Me | Me | Cl | Cl | S | MeNH | 146–148 | 317 | | Example 1 |
| 39 | — | (single bond) | OH | Me | Me | Cl | Cl | O | PhNH | 169–171 | 363 | | Example 1 |
| 40 | — | (single bond) | OH | Me | Me | Cl | CN | S | MeNH | 212–214 | 308 | | Example 1 |
| 41 | — | (single bond) | OH | Me | Me | Cl | Cl | S | MeS | 119–121 | 334 | | Example 1 |
| 42 | — | (single bond) | OH | Me | Me | Cl | Cl | S | p-MeOPhNH | 169–170 | 409 | | Example 1 |
| 43 | — | (single bond) | OH | Me | Me | Cl | Cl | S | PhNH | 142–143 | 379 | | Example 1 |
| 44 | — | (single bond) | OH | Me | Me | H | NO$_2$ | S | MeNH | 148–149 | 294 | | Example 1 |
| 45 | — | (single bond) | OH | Me | Et | H | CN | S | MeNH | 136–139 | 288 | | Example 1 |
| 46 | — | (single bond) | OH | Me | Me | H | SO$_2$Ph | S | MeNH | 182–183 | 389 | | Example 1 |
| 47 | — | (single bond) | OH | Me | Me | H | CN | S | EtNH | 134–136 | 288 | | Example 1 |
| 48 | — | (single bond) | OH | Me | Me | H | CN | O | EtO | 124–125 | 273 | | Example 1 |
| 49 | — | (single bond) | OH | Me | Me | H | OMe | S | MeNH | 123–124 | 279 | | Example 1 |
| 50 | — | (single bond) | OH | Me | Me | H | CN | S | Me$_2$CHCH$_2$NH | 124–126 | 316 | | Example 1 |
| 51 | — | (single bond) | OH | Me | Me | H | CN | S | p-MeOPhNH | 173–175 | 366 | | Example 1 |
| 52 | — | (single bond) | OH | Me | Me | H | CN | O | EtNH | 126–127 | 272 | | Example 1 |
| 53 | — | (single bond) | OH | Me | Me | H | NO$_2$ | O | MeNH | 200–201 | 258 | | Example 1 |
| 54 | — | (single bond) | OH | Me | Me | H | CN | O | MeNH | 151–152 | 278 | | Example 1 |
| 55 | Me | =O | | Me | Me | H | CN | S | MeNH | 157.5–159 | 288 | | Example 1 |
| 56 | H | =O | | Me | Me | H | CN | S | Me$_2$N | 127–129 | 288 | | Example 1 |
| 57 | — | (single bond) | OH | Et | Me | H | NO$_2$ | S | MeNH | 172–173 | 294 | | Example 1 |
| 58 | — | (single bond) | OH | t-Bu | H | H | NO$_2$ | O | MeNH | 174–176 | 322 | | Example 1 |
| 59 | — | (single bond) | OH | Me | n-Pr | H | NO$_2$ | O | MeNH | 141–142 | 322 | | Example 1 |
| 60 | — | (single bond) | OH | —(CH$_2$)$_3$— | | H | NO$_2$ | O | MeNH | 177–178 | 306 | | Example 1 |
| 61 | — | (single bond) | OH | —(CH$_2$)$_5$— | | H | NO$_2$ | S | MeNH | 205–208 | 334 | | Example 1 |
| 62 | — | (single bond) | OH | Me | Me | Cl | CN | O | Me$_2$CHNH | 122–124 | 286 | | Example 1 |
| 63 | — | (single bond) | OH | Me | Me | Cl | Cl | O | MeNH | 125–126 | 301 | | Example 1 |
| 64 | — | (single bond) | OH | Me | Me | NO$_2$ | NHCOMe | O | MeNH | 189–193 | 335 | | Example 1 |
| 65 | — | (single bond) | OH | Me | Me | =N—O—N= | | S | MeNH | 150–152 | 275 | | Example 1 |
| 66 | — | (single bond) | OH | Me | Me | H | Et | S | MeNH | 125–127 | 277 | | Example 1 |
| 67 | — | (single bond) | OH | Me | Me | H | CF$_3$ | O | MeNH | 144–145 | 317 | | Example 1 |
| 68 | — | (single bond) | OH | Me | Me | NO$_2$ | H | S | MeNH | 156–158 | 294 | | Example 1 |
| 69 | — | (single bond) | =O | Me | Me | H | Br | O | MeNH | 132–134 | 311 | | Example 1 |
| 70 | Ph | (single bond) | OH | Me | Me | Cl | CN | S | MeNH | 236.5–238 | 350 | | Example 1 |
| 71* | H (cis form) | OH | H | Me | Me | Cl | Cl | S | MeNH | 156–157 | 319 | | Example 2 |
| 72* | H (trans form) | OH | H | Me | Me | Cl | Cl | S | MeNH | 183–185 | 319 | | Example 2 |
| 73 | H | OH | H | Me | Me | Cl | CN | S | MeNH | 181–183 | 310 | | Example 2 |
| 74 | H | OH | H | Me | Me | Cl | CN | S | MeNH | 210–212 | 310 | | Example 2 |
| 75 | H | OH | H | Me | Me | H | NO$_2$ | S | MeNH | 203–207 | 296 | | Example 2 |
| 76 | H | OH | H | Me | Me | H | SO$_2$Ph | S | MeNH | 183–184 | 391 | | Example 2 |

TABLE 2-continued (I)

| Compound No. | R1 | R2 | R3 | R4 | R5 | R6 | R7 | X | Y | Melting Point (°C) | MS (M+) | IR (KBr) (cm⁻¹) | Process of Synthesis |
|---|---|---|---|---|---|---|---|---|---|---|---|---|---|
| 77 | Me | OH | H | Me | Me | H | CN | S | MeNH | 248-250 | 290 | | Example 2 |
| 78 | H | OH (cis form) | H | Me | Me | H | CN | O | MeNH | 188-189 | 260 | | Example 2 |
| 79 | H | OH (trans form) | H | Me | Me | H | CN | O | MeNH | 210-211 | 260 | | Example 2 |
| 80 | — | (single bond) | H | Me | Me | H | NO2 | O | MeNH | 209-211 | 280 | | Example 3 |
| 81 | — | (single bond) | H | Me | Me | H | CN | O | Me2CHNH | 188-189 | 288 | | Example 3 |
| 82 | — | (single bond) | H | Me | Me | Cl | Cl | S | MeNH | 155-156 | 301 | | Example 3 |
| 83 | — | (single bond) | H | Me | Me | Cl | CN | S | MeNH | 144-145 | 292 | | Example 3 |
| 84 | — | (single bond) | H | Me | Me | H | SO2Ph | S | MeNH | 93-95 | 373 | | Example 3 |
| 85 | — | (single bond) | H | Me | Me | H | CN | O | MeNH | 198-199 | 242 | | Example 3 |
| 86 | — | (single bond) | H | Me | Me | H | NO2 | S | MeNH | 165-166 | 262 | | Example 3 |
| 87 | — | (single bond) | H | Me | Me | H | CN | O | p-ClPhNH | 160-162 | 354 | | Example 3 |
| 88 | — | (single bond) | H | Me | Me | H | COOMe | S | MeNH | 207-208 | 291 | | Example 3 |
| 89 | — | (single bond) | H | Me | Me | H | SO2Me | S | MeMH | 138-139 | 311 | | Example 3 |
| 90 | — | (single bond) | H | Me | Me | H | NO2 | S | MeNH | 139-140 | 292 | | Example 3 |
| 91 | — | (single bond) | H | Me | Et | H | NO2 | S | MeNH | 212-215 | 318 | | Example 3 |
| 92 | — | (single bond) | —(CH2)5— | | Me | H | Et | S | MeNH | 110-111 | 261 | | Example 3 |
| 93 | — | (single bond) | —(CH2)6— | | Me | H | NO2 | S | MeNH | 158-159 | 332 | | Example 3 |
| 94 | — | (single bond) | H | Me | Me | H | Cl | O | PhNH | 206-207 | 347 | | Example 7 |
| 95 | — | (single bond) | H | Me | Me | Cl | Cl | S | p-MeOPhNH | 133-134 | 393 | | Example 7 |
| 96 | — | (single bond) | H | Me | Me | Cl | Cl | S | PhNH | 133-134 | 363 | | Example 7 |
| 97 | — | (single bond) | H | Me | Me | H | OMe | O | EtNH | 173-174 | 256 | | Example 7 |
| 98 | — | (single bond) | H | Me | Me | H | CN | S | MeNH | 107-108 | 263 | | Example 7 |
| 99 | — | (single bond) | H | Me | Me | H | CN | S | Me2CHCH2NH | 102-106 | 300 | | Example 7 |
| 100 | — | (single bond) | H | Me | Me | H | CN | S | p-MeOPhNH | — | 350 | 2224 (CN) | Example 7 |
| 101 | — | (single bond) | H | Me | Me | H | CN | S | PhNH | 153-156 | 320 | | Example 7 |
| 102 | — | (single bond) | H | Me | Me | H | CN | O | PhNH | 242-243 | 304 | | Example 7 |
| 103 | — | (single bond) | H | Me | Me | H | Cl | S | MeNH | 138-140 | 267 | | Example 9 |
| 104 | — | (single bond) | H | Me | Me | H | CF3 | S | MeNH | 150-151 | 301 | | Example 9 |
| 105 | — | (single bond) | H | Me | Me | H | OCF3 | S | MeNH | 124-125 | 317 | | Example 9 |
| 106 | — | (single bond) | H | Me | Me | H | SO2Me | S | MeNH | 151-152 | 325 | | Example 9 |
| 107 | — | (single bond) | H | Me | Me | H | CN | S | Me2N | 172-173 | 272 | | Example 9 |
| 108 | — | (single bond) | H | Me | Me | H | CN | S | Me2N | 172-174 | 286 | | Example 9 |
| 109 | — | (single bond) | H | Me | Me | H | CN | S | Me2CHNH | 156-158 | 354 | | Example 9 |
| 110 | — | (single bond) | H | Me | Me | H | CN | S | m-ClPhNH | 146.5-148 | 354 | | Example 9 |
| 111 | — | (single bond) | —(CH2)4— | | Me | H | CN | S | o-ClPhNH | 196-197 | 284 | | Example 9 |
| 112 | — | (single bond) | H | Me | Me | H | NO2 | S | NH2 | 151-152 | 264 | | Example 9 |
| 113 | — | (single bond) | H | Me | Me | H | NO2 | S | EtNH | 149.5-151 | 292 | | Example 9 |
| 114 | — | (single bond) | H | Me | Me | H | NO2 | S | Et2N | 130-132 | 320 | | Example 9 |

TABLE 2-continued (I)

| Compound No. | R₁ | R₂ | R₃ | R₄ | R₅ | R₆ | R₇ | X | Y | Melting Point (°C.) | MS (M⁺) | IR (KBr) (cm⁻¹) | Process of Synthesis |
|---|---|---|---|---|---|---|---|---|---|---|---|---|---|
| 115 | — | (single bond) | H | Me | Me | H | NO₂ | S | n-PrNH | 101–102 | 306 | | Example 9 |
| 116 | — | (single bond) | H | Me | Me | H | NO₂ | S | Me₂CHNH | 145–147 | 306 | | Example 9 |
| 117 | — | (single bond) | H | Me | Me | H | NO₂ | S | n-BuNH | 119–121 | 320 | | Example 9 |
| 118 | — | (single bond) | H | Me | Me | H | NO₂ | S | HOCH₂CH₂NH | 154–156 | 308 | | Example 9 |
| 119 | — | (single bond) | H | Me | Me | H | NO₂ | S | MeNCHMe₂ | 143.5–145 | 320 | | Example 9 |
| 120 | — | (single bond) | H | Me | Me | H | NO₂ | S | PhNH | 152.5–155 | 340 | | Example 9 |
| 121 | — | (single bond) | H | Me | Me | H | NO₂ | S | ![azetidine] | 153–154 | 304 | | Example 9 |
| 122 | — | (single bond) | H | Me | Me | H | NO₂ | S | ![piperidine] | 180–181 | 318 | | Example 9 |
| 123 | — | (single bond) | H | Me | Me | H | NO₂ | S | ![piperidine] | 171–173 | 332 | | Example 9 |
| 124 | — | (single bond) | H | Me | Me | H | NO₂ | S | t-Bu-O-CHN(C=O)-piperidinyl | 186–187 | 433 | | Example 9 |
| 125 | — | (single bond) | H | t-Bu | H | H | NO₂ | S | MeNH | 156–157 | 306 | — | Example 9 |
| 126 | — | (single bond) | H | Et | Et | H | NO₂ | S | MeNH | 127–128 | 306 | | Example 9 |
| 127 | — | (single bond) | H | —(CH₂)₃— | | H | NO₂ | S | MeNH | 165–166 | 290 | | Example 9 |
| 128 | — | (single bond) | H | —(CH₂)₄— | | H | NO₂ | S | MeNH | 191–192 | 304 | | Example 9 |
| 129 | — | (single bond) | H | Me | Me | H | NO₂ | S | NH₂ | 160–162 | 261 | | Example 9 |
| 130 | — | (single bond) | H | Me | Me | =N—O—N= | S | MeNH | 215–216 | 275 | | Example 9 |
| 131 | — | (single bond) | H | Me | Me | =N—O—N= | S | Me₂N | 160–161 | 289 | | Example 9 |
| 132 | — | (single bond) | H | Me | Me | H | NO₂ | S | MeMEt | 100–103 | 306 | | Example 9 |
| 133 | — | (single bond) | H | Me | Me | H | NO₂ | S | MeNCH₂Ph | 162–163 | 368 | | Example 9 |

TABLE 2-continued

(I)

| Compound No. | R1 | R2 | R3 | R4 | R5 | R6 | R7 | X | Y | Melting Point (°C.) | MS (M+) | IR (KBr) (cm⁻¹) | Process of Synthesis |
|---|---|---|---|---|---|---|---|---|---|---|---|---|---|
| 134 | — | (single bond) | H | Me | Me | H | Br | S | MeNH | 136–138 | 311 | | Example 9 |
| 135 | — | (single bond) | H | Me | Me | H | NO2 | S | MeN⟨piperidine⟩ | 158–159 | 347 | | Example 9 |
| 136 | — | (single bond) | H | Me | Me | H | NO2 | S | morpholine | 184–186 | 334 | | Example 9 |
| 137 | — | (single bond) | H | Me | Me | H | NO2 | S | cyc-PrNH | 121–123 | 304 | | Example 9 |
| 138 | — | (single bond) | H | Me | Me | H | NO2 | S | t-BuOCOCH2NH | 142–143 | 378 | | Example 9 |
| 139 | — | (single bond) | H | Me | Me | H | NO2 | S | Me2N | 139–141 | 292 | | Example 9 |
| 140 | — | (single bond) | H | Me | Me | Cl | CN | NCN | Me2N | 193–194 | 314 | | Example 10(3) |
| 141 | — | (single bond) | H | Me | Me | H | CN | NCN | Me2N | 219–221 | 280 | | Example 10(3) |
| 142 | — | (single bond) | H | Me | Me | H | NO2 | O | NCNH | 178–180 | 273 | | Example 13 |
| 143 | — | (single bond) | H | Me | Me | H | NO2 | O | MeONH | 161–163 | 278 | | Example 13 |
| 144 | — | (single bond) | H | Me | Me | H | NO2 | O | MeONH | 162–163 | 278 | | Example 13 |
| 145 | — | (single bond) | H | Me | Me | H | NO2 | O | HOCH2CH2NH | 157.5–159 | 292 | | Example 13 |
| 146 | — | (single bond) | H | Me | Me | H | NO2 | O | n-PrNH | 143–144 | 290 | | Example 13 |
| 147 | — | (single bond) | H | Me | Me | H | NO2 | O | n-BuNH | 92–93 | 304 | | Example 13 |
| 148 | — | (single bond) | H | Me | Me | H | NO2 | O | cyc-PrNH | 143–146 | 288 | | Example 13 |
| 149 | — | (single bond) | H | Me | Me | H | NO2 | O | t-BuOCOCH2NH | 180–182 | 362 | | Example 13 |
| 150 | — | (single bond) | H | Me | Me | H | NO2 | O | n-Pr2N | 73–74 | 332 | | Example 13 |
| 151 | — | (single bond) | H | Me | Me | H | NO2 | O | i-Pr2N | 117–119 | 278 | | Example 13 |
| 152 | — | (single bond) | H | Me | Me | H | NO2 | O | n-Bu2N | oily | 360 | 1630 (C=O) | Example 13 |
| 153 | — | (single bond) | H | Me | Me | H | NO2 | O | Ph2N | 163–164 | 400 | | Example 13 |
| 154 | — (single bond) | H | Me | Me | H | NO2 | O | azetidinyl | 149–150 | 288 | | Example 13 |

TABLE 2-continued (I)

| Compound No. | R₁ | R₂ | R₃ | R₄ | R₅ | R₆ | R₇ | X | Y | Melting Point (°C.) | MS (M+) | IR (KBr) (cm⁻¹) | Process of Synthesis |
|---|---|---|---|---|---|---|---|---|---|---|---|---|---|
| 155 | — | (single bond) | H | Me | Me | H | NO₂ | O | piperidine (N) | 195-196 | 302 | | Example 13 |
| 156 | — | (single bond) | H | Me | Me | H | NO₂ | O | —O—C(Me)₂—CHN(piperidine)=O | 130-135 | 417 | | Example 13 |
| 157 | — | (single bond) | H | Me | Me | H | NO₂ | O | piperidine (N) | 189-191 | 316 | | Example 13 |
| 158 | — | (single bond) | H | Me | Me | H | NO₂ | O | morpholine (N, O) | 189-192 | 318 | | Example 13 |
| 159 | — | (single bond) | H | Me | Me | H | NO₂ | O | N-methylpiperazine (MeN, N) | 235-237 | 331 | | Example 13 |
| 160 | — | (single bond) | H | Me | Me | H | NO₂ | O | 2,5-dimethylpyrrolidine (N) | 177-178 | 330 | | Example 13 |
| 161 | — | (single bond) | H | Me | Me | =N—O—N= | =N—O—N= | O | MeNH | 201-202 | 259 | | Example 13 |
| 162 | — | (single bond) | H | Me | Me | =N—O—N= | =N—O—N= | O | Me₂N | 177-178 | 273 | | Example 13 |

TABLE 2-continued (structure I with R1, R2, R3, R4, R5 on chroman and R6, R7 on aromatic ring, with X=C(Y))

| Compound No. | R1 | R2 | R3 | R4 | R5 | R6 | R7 | X | Y | Melting Point (°C.) | MS (M+) | IR (KBr) (cm⁻¹) | Process of Synthesis |
|---|---|---|---|---|---|---|---|---|---|---|---|---|---|
| 163 | — | (single bond) | H | Me | Me | H | $NO_2$ | NCN | $MeNCH_2CH_2OH$ | 158–159 | 330 | | Example 14 |
| 164 | — | (single bond) | H | Me | Me | H | $NO_2$ | NCN | $HNCH_2CH_2OH$ | 174.5–175.5 | 316 | | Example 14 |
| 165 | — | (single bond) | H | Me | Me | H | Br | O | MeNH | 157–160 | 295 | | Example 10(3) |
| 166 | — | (single bond) | H | Me | Me | Cl | Cl | O | MeNH | 172–173 | 285 | | Example 10(3) |
| 167 | — | (single bond) | H | Me | Me | H | CN | O | $Me_2CHNH$ | 135–137 | 270 | | Example 10(3) |
| 168 | — | (single bond) | H | Me | Me | H | CN | O | m-ClPhNH | 240.5–241.5 | 338 | | Example 10(3) |
| 169 | — | (single bond) | H | Me | Me | H | CN | O | o-ClPhNH | 231–232.5 | 338 | | Example 10(3) |
| 170 | — | (single bond) | H | Me | Me | H | $NO_2$ | O | $NH_2$ | 144–145 | 248 | | Example 10(3) |
| 171 | — | (single bond) | H | Me | Me | H | $NO_2$ | O | $Me_2CHNH$ | 119–120 | 290 | | Example 10(3) |
| 172 | — | (single bond) | H | Me | Me | H | H | O | MeNH | 161–163 | 217 | | Example 15 |
| 173 | — | (single bond) | H | Me | Me | H | Cl | O | MeNH | 166–167 | 251 | | Example 15 |
| 174 | — | (single bond) | H | Me | Me | H | $OCF_3$ | O | MeNH | 159–160 | 301 | | Example 15 |
| 175 | — | (single bond) | H | Me | Me | H | $SO_2Me$ | O | MeNH | 76–78 | 295 | | Example 15 |
| 176 | — | (single bond) | H | Me | Me | H | COOMe | O | MeNH | 110–111 | 275 | | Example 15 |
| 177 | — | (single bond) | H | Me | Me | H | CN | O | MeNH | 196–197 | 268 | | Example 15 |
| 178 | — | (single bond) | H | Me | —$(CH_2)_4$— | H | $NO_2$ | O | MeNH | 153–155 | 276 | | Example 15 |
| 179 | — | (single bond) | H | Et | Me | H | $NO_2$ | O | EtNH | 157–159 | 262 | | Example 15 |
| 180 | — | (single bond) | H | t-Bu | H | H | $NO_2$ | O | MeNH | 156–157 | 290 | | Example 15 |
| 181 | — | (single bond) | H | Me | Et | H | $NO_2$ | O | MeNH | 144–145 | 276 | | Example 15 |
| 182 | — | (single bond) | H | Et | n-Pr | H | $NO_2$ | O | MeNH | 127–129 | 290 | | Example 15 |
| 183 | — | (single bond) | H | Me | —$(CH_2)_3$— | H | $NO_2$ | O | MeNH | 143–144 | 274 | | Example 15 |
| 184 | — | (single bond) | H | —$(CH_2)_4$— | Me | H | $NO_2$ | O | MeNH | 228–229 | 288 | | Example 15 |
| 185 | — | (single bond) | H | —$(CH_2)_5$— | Me | H | $NO_2$ | O | MeNH | 208–209 | 302 | | Example 15 |
| 186 | — | (single bond) | H | —$(CH_2)_6$— | Me | H | $NO_2$ | O | MeNH | 172–173 | 316 | | Example 15 |
| 187 | — | (single bond) | H | Me | Me | Cl | CN | O | MeNH | 171–172 | 276 | | Example 15 |
| 188 | — | (single bond) | H | Me | Me | H | $SO_2Ph$ | O | MeNH | 158–159 | 357 | | Example 16 |
| 189 | — | (single bond) | H | Me | Me | H | $NO_2$ | O | PhNH | 211–212 | 324 | | Example 16 |
| 190 | — | (single bond) | H | Me | Me | H | CN | O | $Me_2N$ | 95–96 | 256 | | Example 17 |
| 191 | — | (single bond) | H | Me | Me | H | $SO_2Me$ | O | $Me_2N$ | 159–161 | 309 | | Example 17 |
| 192 | — | (single bond) | H | Me | Me | H | $NO_2$ | O | $Et_2N$ | 75–76 | 304 | | Example 17 |
| 193 | — | (single bond) | H | Me | Me | H | $NO_2$ | O | $MeNCHMe_2$ | 141–142 | 304 | | Example 17 |
| 194 | — | (single bond) | H | Me | Me | H | $NO_2$ | O | MeNOMe | 96–98 | 292 | | Example 17 |
| 195 | — | (single bond) | H | Me | Me | H | $NO_2$ | O | EtNOMe | 63–65 | 306 | | Example 17 |
| 196 | — | (single bond) | H | Me | Me | H | $NO_2$ | O | $MeNCH_2Ph$ | 114–116 | 352 | | Example 17 |
| 197 | — | (single bond) | H | Me | Me | H | $NO_2$ | NCN | MeNCN | 123–124 | 287 | | Example 21 |
| 198 | — | (single bond) | H | Me | Me | H | $NO_2$ | NCN | NCNH | 281–284 | 297 | | Example 21 |
| 199 | — | (single bond) | H | Me | Me | H | $NO_2$ | NCN | MeNOMe | 145–146 | 316 | | Example 21 |
| 200 | — | (single bond) | H | Me | Me | H | $NO_2$ | NCN | $CF_3CH_2NH$ | 204–205 | 354 | | Example 21 |
| 201 | — | (single bond) | H | Me | Me | H | $NO_2$ | NCN | t-BuNH | 235–237 | 328 | | Example 21 |
| 202 | — | (single bond) | H | Me | Me | H | $NO_2$ | NCN | i-BuNH | 200–201 | 328 | | Example 21 |

TABLE 2-continued (I)

| Compound No. | R₁ | R₂ | R₃ | R₄ | R₅ | R₆ | R₇ | X | Y | Melting Point (°C.) | MS (M⁺) | IR (KBr) (cm⁻¹) | Process of Synthesis |
|---|---|---|---|---|---|---|---|---|---|---|---|---|---|
| 204 | — | (single bond) | H | Me | Me | H | NO₂ | NCN | t-BuCH₂NH | 187–188 | 342 | | Example 21 |
| 205 | — | (single bond) | H | Me | Me | H | NO₂ | NCN | cyc-PenNH | 203–205 | 340 | | Example 21 |
| 206 | — | (single bond) | H | Me | Me | H | NO₂ | NCN | t-BuOCOCH₂NH | 181–182 | 386 | | Example 21 |
| 207 | — | (single bond) | H | Me | Me | H | NO₂ | NCN | HOCH₂CH(Me)NH | 163–164 | 330 | | Example 21 |
| 208 | — | (single bond) | H | Me | Me | H | NO₂ | NCN | PhCH₂NH | 193–195 | 362 | | Example 21 |
| 209 | — | (single bond) | H | Me | Me | H | NO₂ | NCN | n-Pr₂N | 162–164 | 356 | | Example 21 |
| 210 | — | (single bond) | H | Me | Me | H | NO₂ | NCN | n-Bu₂N | 141–142 | 384 | | Example 21 |
| 211 | — | (single bond) | H | Me | Me | H | NO₂ | NCN | MeN⟨piperidine⟩ | 176–178 | 355 | | Example 21 |
| 212 | | H | H | Me | Me | H | CN | S | MeNH | 174–175 | 260 | | Example 22 |
| 213 | | H | OH | Me | Me | H | NO₂ | S | MeNH | 161–162 | 280 | | Example 22 |
| 214 | — | (single bond) | OH | Me | Me | H | CN | O | NHOMe | 160.5–163 | 274 | | Example 29 |
| 215 | — | (single bond) | H | Me | Me | H | CN | O | NH₂ | 208–210 | 244 | | Example 29 |
| 216 | — | (single bond) | H | Me | Me | H | Cl | NCN | Me₂N | 167–168 | 289 | | Example 36 |
| 217 | — | (single bond) | H | Me | Me | H | Br | NCN | Me₂N | 164–165 | 333 | | Example 36 |
| 218 | — | (single bond) | H | Me | Me | H | CF₃ | NCN | Me₂N | 132–133 | 323 | | Example 36 |
| 219 | — | (single bond) | H | Me | Me | H | SO₂Me | NCN | Me₂N | 246–247 | 333 | | Example 36 |
| 220 | — | (single bond) | H | Me | Me | H | SO₂Ph | NCN | Me₂N | 200–201 | 395 | | Example 36 |
| 221 | — | (single bond) | H | Me | Me | H | =N—O—N= | NCN | Me₂N | 186–187 | 297 | | Example 36 |
| 222 | — | (single bond) | H | Me | Me | H | NO₂ | NCN | Et₂N | 159–161 | 328 | | Example 36 |
| 223 | — | (single bond) | H | Me | Me | H | NO₂ | NCN | MeNCHMe₂ | 165–166 | 328 | | Example 36 |
| 224 | — | (single bond) | H | Me | Me | H | NO₂ | NCN | MeNEt | 151–152 | 314 | | Example 36 |
| 225 | — | (single bond) | H | Me | Me | H | NO₂ | NCN | MeNCH₂Ph | 183–186 | 376 | | Example 36 |
| 226 | — | (single bond) | H | Me | Me | H | NO₂ | NCN | MeN(CH₂)₂OSiMe₂(t-Bu) | 157–158 | 444 | | Example 36 |
| 227 | — | (single bond) | H | Me | Me | H | NO₂ | NCN | MeNCH₂COOEt | 149–150 | 372 | | Example 36 |
| 228 | — | (single bond) | H | Me | Me | H | NO₂ | NCN | ⟨azetidine-N⟩ | 240–243 | 312 | | Example 36 |

TABLE 2-continued

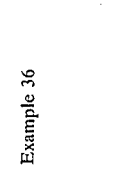

(I)

| Compound No. | R₁ | R₂ | R₃ | R₄ | R₅ | R₆ | R₇ | X | Y | Melting Point (°C.) | MS (M⁺) | IR (KBr) (cm⁻¹) | Process of Synthesis |
|---|---|---|---|---|---|---|---|---|---|---|---|---|---|
| 229 | — | (single bond) | H | Me | Me | H | NO₂ | NCN | 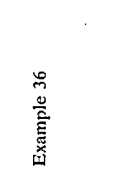 | 213–214 | 326 | | Example 36 |
| 230 | — | (single bond) | H | Me | Me | H | NO₂ | NCN | 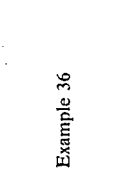 | 183–184 | 441 | | Example 36 |
| 231 | — | (single bond) | H | Me | Me | H | NO₂ | NCN |  | 181–182 | 456 | | Example 36 |
| 232 | — | (single bond) | H | Me | Me | H | NO₂ | NCN | 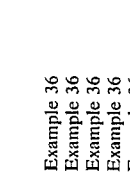 | 182–183 | 340 | | Example 36 |
| 233 | — | (single bond) | H | Me | Me | H | NO₂ | NCN | 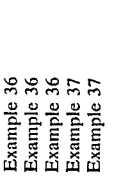 | 183–184 | 342 | | Example 36 |
| 234 | — | (single bond) | H | Et | H | H | NO₂ | NCN | Me₂N | 159–161 | 300 | | Example 36 |
| 235 | — | (single bond) | H | t-Bu | H | H | NO₂ | NCN | Me₂N | 220–221 | 328 | | Example 36 |
| 236 | — | (single bond) | H | Me | Et | H | NO₂ | NCN | Me₂N | 160–161 | 314 | | Example 36 |
| 237 | — | (single bond) | H | Me | n-Pr | H | NO₂ | NCN | Me₂N | 97–100 | 328 | | Example 36 |
| 238 | — | (single bond) | H | Et | Et | H | NO₂ | NCN | Me₂N | 130–131 | 328 | | Example 36 |
| 239 | — | (single bond) | H | —(CH₂)₄— | | H | NO₂ | NCN | Me₂N | 218–219 | 326 | | Example 36 |
| 240 | — | (single bond) | H | —(CH₂)₅— | | H | NO₂ | NCN | Me₂N | 203–204 | 340 | | Example 36 |
| 241 | — | (single bond) | H | Me | Me | H | Br | NCN | MeNH | 215–216 | 319 | | Example 37 |
| 242 | — | (single bond) | H | Me | Me | Cl | CN | NCN | MeNH | 275–276 | 300 | | Example 37 |

TABLE 2-continued $$\begin{array}{c} \phantom{X=C}R_1\ R_2\ R_3\ R_4\ R_5 \\ X=C \\ R_7\ R_6\ O \end{array} \quad (I)$$

| Compound No. | R₁ | R₂ | R₃ | R₄ | R₅ | R₆ | R₇ | X | Y | Melting Point (°C.) | MS (M+) | IR (KBr) (cm⁻¹) | Process of Synthesis |
|---|---|---|---|---|---|---|---|---|---|---|---|---|---|
| 243 | — | (single bond) | H | Me | Me | H | SO₂Me | NCN | MeNH | 234–235 | 319 | | Example 37 |
| 244 | — | (single bond) | H | Me | Me | H | SO₂Ph | NCN | MeNH | 118–120 | 381 | | Example 37 |
| 245 | — | (single bond) | H | Me | Me | H | NO₂ | NCN | EtNH | 198–200 | 300 | | Example 37 |
| 246 | — | (single bond) | H | Me | Me | H | NO₂ | NCN | Me₂CHNH | 237–239 | 314 | | Example 37 |
| 247 | — | (single bond) | H | Me | Et | H | CN | NCN | MeNH | 213–214 | 300 | | Example 37 |
| 248 | — | (single bond) | H | t-Bu | H | H | NO₂ | NCN | MeNH | 261–263 | 266 | | Example 37 |
| 249 | — | (single bond) | H | Me | Me | H | CN | NCN | MeNH | 221–223 | 314 | | Example 37 |
| 250 | — | (single bond) | OH | Me | Me | H | SO₂Me | S | MeNH | 103–104 | 327 | | Example 1 |
| 251 | — | (single bond) | OH | Me | Me | H | Cl | S | MeNH | 137–138 | 283 | | Example 1 |
| 252 | — | (single bond) | OH | Me | Me | H | OCF₃ | S | MeNH | 92–93 | 333 | | Example 1 |
| 253 | — | (single bond) | OH | Me | Et | H | NO₂ | S | MeNH | 189–190 | 308 | | Example 1 |
| 254 | — | (single bond) | OH | Et | Et | H | NO₂ | S | MeNH | 217–218 | 322 | | Example 1 |
| 255 | — | (single bond) | OH | —(CH₂)₄— | | H | NO₂ | S | MeNH | 206–207 | 320 | | Example 1 |
| 256 | — | (single bond) | OH | —(CH₂)₆— | | H | CN | S | MeNH | 190–193 | 348 | | Example 1 |
| 257 | — | (single bond) | OH | —(CH₂)₄— | | H | NO₂ | S | MeNH | 186–189 | 300 | | Example 1 |
| 258 | — | (single bond) | H | Me | n-Pr | H | NO₂ | S | MeNH | oily | 306 | 1512 (NO₂) 1340 (NO₂) | Example 3 |
| 259 | — | (single bond) | H | Me | Me | H | NO₂ | S | n-Pr₂N | 111–113 | 348 | | Example 9 |
| 260 | — | (single bond) | H | Me | Me | H | OCF₃ | NCN | Me₂N | 123–124 | 339 | | Example 36 |
| 261 | — | (single bond) | H | Me | Me | Cl | Cl | NCN | Me₂N | 149–151 | 324 | | Example 36 |
| 262 | — | (single bond) | H | —(CH₂)₄— | | H | CN | NCN | Me₂N | 256–258 | 306 | | Example 36 |
| 263 | — | (single bond) | H | —(CH₂)₆— | | H | NO₂ | NCN | Me₂N | 196–197 | 354 | | Example 36 |
| 264 | — | (single bond) | H | Me | Me | H | OCF₃ | CHNO₂ | Me₂N | 217–219 | 319 | | Example 36 |
| 265 | — | (single bond) | H | Me | Me | H | Cl | NCN | MeNH | 151–152 | 325 | | Example 37 |
| 266 | — | (single bond) | H | Me | Me | H | Cl | NCN | MeNH | 203–204 | 275 | | Example 37 |
| 267 | — | (single bond) | H | Me | Me | Cl | NO₂ | NCN | MeNH | 205–208 | 310 | | Example 37 |
| 268 | — | (single bond) | H | Me | Me | H | NO₂ | NCN | MeNH | 152–154 | 314 | | Example 37 |
| 269 | — | (single bond) | H | Et | Et | H | NO₂ | NCN | MeNH | 192–193 | 314 | | Example 37 |
| 270 | — | (single bond) | H | —(CH₂)₄— | | H | NO₂ | NCN | MeNH | 227–229 | 312 | | Example 37 |
| 271 | — | (single bond) | H | —(CH₂)₆— | | H | NO₂ | NCN | MeNH | 229–231 | 340 | | Example 37 |
| 272 | — | (single bond) | H | —(CH₂)₄— | | H | CN | NCN | MeNH | 255–257 | 292 | | Example 37 |
| 273 | — | (single bond) | H | Me | Me | H | =N—O—N= | NCN | MeNH | 250–252 | 283 | | Example 37 |
| 274 | — | (single bond) | H | Me | Me | H | NO₂ | NCN | NH₂CONHNH | 183–187 | 330 | | Example 21 |
| 275 | — | (single bond) | H | Me | Me | H | NO₂ | O | N─────N<br>‖<br>S⟩NH | 292–295 | 332 | | Example 13 |

TABLE 2-continued (I)

| Compound No. | R₁ | R₂ | R₃ | R₄ | R₅ | R₆ | R₇ | X | Y | Melting Point (°C.) | MS (M⁺) | IR (KBr) (cm⁻¹) | Process of Synthesis |
|---|---|---|---|---|---|---|---|---|---|---|---|---|---|
| 276 | — | (single bond) | H | Me | Me | H | NO₂ | O | 2-PyNH | 97-101 | 325 | | Example 13 |
| 277 | — | (single bond) | H | Me | Me | H | NO₂ | O | 3-PyNH | 186-188 | 325 | | Example 13 |
| 278 | — | (single bond) | H | Me | Me | H | NO₂ | O | (thiazoline-NH) | 207-210 | 331 | | Example 13 |
| 279 | — | (single bond) | H | Me | Me | H | NO₂ | O | BrCH₂CH₂NH | 150-152 | 354 | | Example 13 |
| 280 | — | (single bond) | H | Me | Me | H | NO₂ | O | (triazole-NH) | 233-236 | 316 | | Example 13 |
| 281 | — | (single bond) | H | Me | Me | H | NO₂ | O | (aziridine-N) | 140-142 | 274 | | Example 13 |
| 282 | — | (single bond) | H | Me | Me | H | NO₂ | O | cyc-HexNH | 141-142 | 330 | | Example 13 |
| 283 | — | (single bond) | H | Me | Me | H | NO₂ | O | CH≡CCH₂NH | 188-190 | 286 | | Example 13 |
| 284 | — | (single bond) | H | Me | Me | H | NO₂ | O | NH₂CONHNH | 206-208 | 306 | | Example 13 |
| 285 | — | (single bond) | H | Me | Me | H | NO₂ | O | cyc-PenNH | 168-170 | 316 | | Example 13 |
| 286 | — | (single bond) | H | Me | Me | H | NO₂ | O | i-BuONH | 161-163 | 320 | | Example 13 |
| 287 | — | (single bond) | H | Me | Me | H | NO₂ | O | MeOCH₂CH₂NH | 112-114 | 306 | | Example 13 |
| 288 | — | (single bond) | H | Me | Me | H | NO₂ | O | NCCH₂CH₂NH | 145-146 | 301 | | Example 13 |
| 289 | — | (single bond) | H | Me | Me | H | NO₂ | O | cyc-BuNH | 157-158 | 302 | | Example 13 |
| 290 | — | (single bond) | H | Me | Me | H | NO₂ | O | NCCH₂NH | 196-197 | 287 | | Example 13 |
| 291 | — | (single bond) | H | Me | Me | H | NO₂ | O | CH₂=CHCH₂NH | 153-155 | 288 | | Example 13 |
| 292 | — | (single bond) | H | Me | Me | H | NO₂ | O | NMe₂CH₂CH₂NH | 113-116 | 319 | | Example 13 |
| 293 | — | (single bond) | H | Me | Me | H | NO₂ | O | PhCH₂ONH | 134-135 | 354 | | Example 13 |
| 294 | — | (single bond) | H | Me | Me | H | NO₂ | O | 4-PyNH | 242-245 | 325 | | Example 13 |
| 295 | — | (single bond) | H | Me | Me | H | NO₂ | O | MeNHCH₂CH₂NH | 122-125 | 305 | | Example 13 |
| 296 | — | (single bond) | H | Me | Me | H | NO₂ | O | Me₂NNH | 140-142 | 291 | | Example 13 |
| 297 | — | (single bond) | H | Me | Me | H | NO₂ | O | cyc-PrCH₂NH | 161-163 | 302 | | Example 13 |
| 298 | — | (single bond) | H | Me | Me | H | NO₂ | O | NH₂CH₂CH₂NH | 143-145 | 291 | | Example 13 |
| 299 | — | (single bond) | H | Me | Me | H | NO₂ | O | FCH₂CH₂NH | 167-169 | 294 | | Example 13 |

TABLE 2-continued (I)

| Compound No. | R₁ | R₂ | R₃ | R₄ | R₅ | R₆ | R₇ | X | Y | Melting Point (°C.) | MS (M⁺) | IR (KBr) (cm⁻¹) | Process of Synthesis |
|---|---|---|---|---|---|---|---|---|---|---|---|---|---|
| 300 | — | (single bond) | H | Me | Me | H | NO₂ | O | MeSCH₂CH₂NH | 117–119 | 322 | | Example 13 |
| 301 | — | (single bond) | H | Me | Me | H | NO₂ | O | MeCOCH₂NH | 170–171 | 304 | | Example 17 |
| 302 | — | (single bond) | H | Me | Me | H | NO₂ | O | EtONH | 139–141 | 292 | | Example 13 |
| 303 | — | (single bond) | H | Me | Me | H | NO₂ | O | n-PrONH | 158–159 | 306 | | Example 13 |
| 304 | — | (single bond) | H | Me | Me | H | NO₂ | O | n-BuONH | 150–151 | 320 | | Example 13 |
| 305 | — | (single bond) | H | Me | Me | H | NO₂ | O |  | 255–257 | 359 | | Example 13 |
| 306 | — | (single bond) | H | Me | Me | H | NO₂ | O | 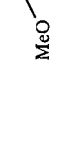 | 175–178 | 355 | | Example 13 |
| 307 | — | (single bond) | H | Me | Me | H | NO₂ | O | 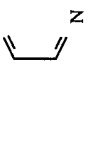 | 96–100 | 326 | | Example 13 |
| 308 | — | (single bond) | H | Me | Me | H | NO₂ | O | 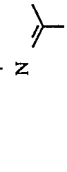 | 268–272 | 342 | | Example 13 |
| 309 | — | (single bond) | OH | —(CH₂)₅— | | H | NO₂ | S | CH₂=CHCH₂NH | 132–136 | 360 | | Example 1 |
| 310 | — | (single bond) | H | —(CH₂)₅— | | H | NO₂ | O | CH₂=CHCH₂NH | 121–122 | 328 | | Example 15 |
| 311 | — | (single bond) | H | Me | Me | H | NO₂ | O |  | 118–123 | 299 | | Example 13 |

TABLE 2-continued
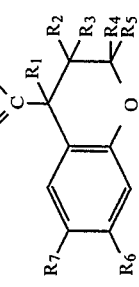
(I)
| Compound No. | R₁ | R₂ | R₃ | R₄ | R₅ | R₆ | R₇ | X | Y | Melting Point (°C.) | MS (M+) | IR (KBr) (cm⁻¹) | Process of Synthesis |
|---|---|---|---|---|---|---|---|---|---|---|---|---|---|
| 312 | — | (single bond) | H | Me | Me | H | NO₂ | O | NH₂NMe | 192-195 | 277 | | Example 13 |
| 313 | — | (single bond) | H | Me | Me | H | NO₂ | O | CH≡CCH₂ONH | 138-140 | 302 | | Example 13 |
| 314 | — | (single bond) | H | Me | Me | H | NO₂ | O | NCCH₂CH₂CH₂NH | — | 315 | 2252 | Example 17 |
| 315 | — | (single bond) | H | Me | Me | H | NO₂ | O | NCCH₂CH₂CH₂NH | — | 329 | 2250 | Example 17 |
*The configurations of 3- and 4-positions of compounds 71 and 72 were not determined Excellent activities of the compounds of the present invention on the $K^+$ channel will now be demonstrated below by way of Test Examples.

TEST EXAMPLE 1

Test with Excised Aorta of Rat

The thoracic aorta was excised from a male Sprague Dawley rat (450 to 600 g) and cut into 2 mm wide ring preparations. Each preparation was suspended in 10 ml of an organ bath containing a Krebs-Henseleit solution (NaCl:119; KCl:4.8; $CaCl_2 \cdot 2H_2O$: 2.53; $KH_2PO_4$:1.2; $MgSO_4 \cdot 7H_2O$: 1.2; $NaHCO_3$: 24.8; glucose: 10 (mM); 37° C.) under a tension of 2 g, and a mixed gas of 95% $O_2$ and 5% $CO_2$ was bubbled therethrough. Isometric contractions of the preparation were recorded by means of an FD pick-up. After equilibrium was reached in 1 to 1.5 hours, 30 mM KCl was added to cause a tissue contraction. The activity of a test compound to relax a lasting contraction following the KCl addition was evaluated by obtaining a 50% inhibitory concentration ($IC_{50}$).

The compounds of the present invention obtained in the foregoing Examples and, for comparison, Cromakalim were used as test compounds. The results obtained are shown in Table 3 below.

TEST EXAMPLE 2

Test with Guinea Pig Tracheal Muscle

The trachea was excised from a male Hartley guinea pig (450 to 550 g) to make chain preparations. The preparation was suspended in a bath containing the same Krebs-Henseleit solution as used in Test Example 1 (37° C.) through which a mixed gas of 95% $O_2$ and 5% $CO_2$ was bubbled. Isometric contractions of the preparation were recorded under a tension of 1 g. The relaxing activity of 1 mM aminophylline on spontaneous tension being taken as 100%, a concentration of a test compound exhibiting 50% relaxing activity ($IC_{50}$) was obtained.

The same test compounds as used in Test Example 1 were used. The results obtained are shown in Table 3.

TABLE 3

| Compound No. | Rat Aorta $IC_{50}$ (M) | Guinea Pig Tracheal Muscle $IC_{50}$ (M) |
|---|---|---|
| 3 | $3.3 \times 10^{-8}$ | $2.0 \times 10^{-7}$ |
| 8 | $1.4 \times 10^{-9}$ | $6.3 \times 10^{-9}$ |
| 10 | $1.1 \times 10^{-8}$ | $3.3 \times 10^{-8}$ |
| 11 | $>3.0 \times 10^{-5}$ | $5.4 \times 10^{-8}$ |
| 12 | $1.1 \times 10^{-8}$ | $2.3 \times 10^{-8}$ |
| 22 | $1.4 \times 10^{-8}$ | $3.6 \times 10^{-8}$ |
| 90 | $1.8 \times 10^{-10}$ | $2.9 \times 10^{-9}$ |
| 91 | $1.4 \times 10^{-10}$ | $3.8 \times 10^{-8}$ |
| 104 | $2.6 \times 10^{-9}$ | $3.7 \times 10^{-8}$ |
| 113 | $3.7 \times 10^{-9}$ | $1.1 \times 10^{-8}$ |
| 115 | $3.0 \times 10^{-9}$ | $4.1 \times 10^{-8}$ |
| 128 | $3.7 \times 10^{-11}$ | $5.0 \times 10^{-8}$ |
| 134 | $9.3 \times 10^{-9}$ | $7.5 \times 10^{-8}$ |
| 137 | $3.7 \times 10^{-9}$ | $2.2 \times 10^{-8}$ |
| 146 | $5.7 \times 10^{-9}$ | $5.6 \times 10^{-8}$ |
| 181 | $2.1 \times 10^{-9}$ | $1.6 \times 10^{-8}$ |
| 186 | $4.2 \times 10^{-11}$ | $1.1 \times 10^{-8}$ |
| 193 | $6.0 \times 10^{-6}$ | $5.7 \times 10^{-8}$ |
| Cromakalim | $1.8 \times 10^{-7}$ | $7.9 \times 10^{-7}$ |

TEST EXAMPLE 3

Study on Antiasthmatic Activity

A mid-line incision was made in the neck of a male Hartley guinea pig (600 to 800 g, CRJ) under anesthesia with pentobarbital (40 mg/kg, i.p.). The trachea, the left carotid vein, and the left carotid artery were exposed, and a cannula was inserted into each of them. The inner pressure of the respiratory tract was measured while applying artificial respiration through the tracheal cannula. The blood pressure was measured through the arterial cannula, and the heart rate was determined from the pulse. Pentobarbital for anesthesia maintenance was continuously administered through the venous cannula. A mid-line incision was made on the abdomen to expose the duodenum, and a cannula for intraduodenal administration was inserted thereinto. After the postoperative convalescence of 30 to 60 minutes, histamine (5 to 10 μg/kg) was intravenously administered every 10 minutes. After it was confirmed that a respiratory tract inner pressure rise reaction was stably obtained, a test compound in the form of a 0.3% CMC suspension was intraduodenally administered. The histamine dose was so selected that the respiratory tract inner pressure might rise to 20 to 40 $cmH_2O$ after every lntravenous administration. After administration of the test compound, intravenous administration of histamine at 10 minutes intervals was continued. The histamine-induced increase in respiratory tract inner pressure after the administration of the test compound was compared with that before the administration.

The activity of the test compound, expressed in terms of dose level required for 50% inhibition of the histamine-induced increase in respiratory tract inner pressure ($ED_{50}$, mg/kg), is shown in Table 4 below.

TABLE 4

| Compound No. | $ED_{50}$ (mg/kg) |
|---|---|
| 8 | 0.1–0.3 |
| 10 | <0.1 |
| 11 | 0.1 |
| 12 | 0.1–0.3 |
| 22 | <0.3 |
| 181 | 0.1–0.3 |
| 193 | <0.3 |
| Cromakalim | 1.0–3.0 |

UTILITY OF THE INVENTION IN INDUSTRY

The novel compounds of the present invention have excellent $K^+$ channel activating activity and are therefore expected to make great contribution to the art, such as medical compositions utilizing $K^+$ channel activation (e.g., anti-asthmatics).

What is claimed is:

1. A benzopyran derivative represented by the formula:

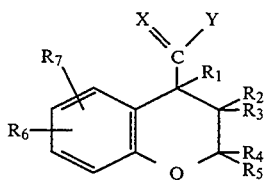

wherein X is an oxygen atom or a sulfur atom, Y represents $-NR_8R_9$ wherein $R_8$ and $R_9$ represent a substituted lower alkyl with the proviso that the substituent is not lower alkyl or a hydrogen atom, provided that at least one of $R_8$ and $R_9$ is a said substituted lower alkyl, $R_1$ represents a hydrogen atom, a lower alkyl group or an aryl group, or it is directly bonded to $R_2$ to form a single bond, $R_2$ and $R_3$, which may be the same or different, each represents a hydrogen atom or a hydroxyl group, or they are taken together to form =O, or $R_2$ is directly bonded to $R_1$ to form a single bond, $R_4$ and $R_5$, which may be the same or different, each represents a hydrogen atom or a lower alkyl group, or they are taken together to form a polymethylene group, and $R_6$ and $R_7$ represent a nitro group or a hydrogen atom, provided that at least one of $R_6$ and $R_7$ is a nitro group.

2. A benzopyran derivative according to claim 1 wherein X is oxygen.

3. A compound according to claim 1 wherein $R_1$ and $R_2$ form a single bond.

4. A compound according to claim 1 wherein $R_3$ is hydrogen.

5. A compound according to claim 1 wherein at least one $R_4$ and $R_5$ is lower alkyl.

6. A compound according to claim 5 wherein both $R_4$ and $R_5$ are methyl.

7. A compound according to claim 1 wherein one of $R_8$ and $R_9$ is hydrogen.

8. A compound according to claim 1 wherein one of $R_8$ and $R_9$ is cyano substituted lower alkyl.

9. A compound according to claim 1 wherein $R_8$ or $R_9$ is —$CH_2CH_2CN$.

10. A compound according to claim 1 wherein X is oxygen; $R_1+R_2$ form a single bond; $R_4$ is hydrogen; $R_3$ and $R_5$ are both methyl; one of $R_6$ and $R_7$ is hydrogen and the other of $R_6$ and $R_7$ is nitro; and one of $R_8$ and $R_9$ is hydrogen and the other of $R_8$ and $R_9$ is —$CH_2CH_2CN$.

* * * * *